(12) United States Patent
Warden et al.

(10) Patent No.: US 7,659,971 B2
(45) Date of Patent: Feb. 9, 2010

(54) LENSOMETERS AND WAVEFRONT SENSORS AND METHODS OF MEASURING ABERRATION

(75) Inventors: Laurence Warden, Poway, CA (US); John Ferro, Santa Rosa, CA (US); Andreas W. Dreher, Escondido, CA (US); William G. Foote, Poway, CA (US)

(73) Assignee: Ophthonix, Inc., Vista, CA (US)

( * ) Notice: Subject to any disclaimer, the term of this patent is extended or adjusted under 35 U.S.C. 154(b) by 0 days.

(21) Appl. No.: 12/019,614

(22) Filed: Jan. 24, 2008

(65) Prior Publication Data
US 2008/0180635 A1    Jul. 31, 2008

Related U.S. Application Data

(63) Continuation of application No. 10/971,937, filed on Oct. 22, 2004, now abandoned.

(60) Provisional application No. 60/581,127, filed on Jun. 18, 2004, provisional application No. 60/520,294, filed on Nov. 14, 2003.

(51) Int. Cl.
*G01B 9/00*  (2006.01)

(52) U.S. Cl. .................................. 356/124

(58) Field of Classification Search .............. None
See application file for complete search history.

(56) References Cited

U.S. PATENT DOCUMENTS

| 4,715,704 | A  | 12/1987 | Biber et al. |
| 5,963,300 | A  | 10/1999 | Horwitz |
| 6,761,454 | B2 | 7/2004 | Lai et al. |
| 6,781,681 | B2 | 8/2004 | Horwitz |
| 6,786,602 | B2 | 9/2004 | Abitbol |

FOREIGN PATENT DOCUMENTS

WO    WO-03/050472    6/2003

*Primary Examiner*—Gregory J Toatley, Jr.
*Assistant Examiner*—Amanda H Merlino
(74) *Attorney, Agent, or Firm*—Morrison & Foerster LLP

(57) ABSTRACT

Wavefront measuring systems and methods are disclosed which may be employed, for example, in detecting phase aberrations in a spectacle lens and in an eye. Various embodiments include disposing a modulation pattern in the path of a return beam from the spectacle lens or the eye, and imaging a diffraction pattern at a self-imaging plane relative to the modulation pattern with a detector. The diffraction pattern is analyzed and the results are used to produce a representation of the wavefront phase characteristics that describe aberrations in the lens or eye being measured. Illumination and processing techniques for improving the measurement results are disclosed. Various embodiments comprise systems adaptable to both measure aberrations in lenses in spectacles as well as in a patient's eyes.

19 Claims, 19 Drawing Sheets

LENSOMETERS AND WAVEFRONT SENSORS AND METHODS OF MEASURING ABERRATION

CROSS-REFERENCE TO RELATED APPLICATIONS

This application is a continuation of U.S. Ser. No. 10/971,937, filed 22 Oct. 2004, which claims benefit of Provisional Application Ser. Nos. 60/581,127, filed 18 Jun. 2004, and 60/520,294, filed 14 Nov. 2003. The contents of these documents are incorporated herein by reference.

FIELD OF THE INVENTION

The invention relates generally to systems and methods for measuring wavefronts such as self-imaging based lensometers and wavefront sensors and methods of measuring aberrations of lenses such as corrective ophthalmic lenses as well as aberrations in the eye.

BACKGROUND

Traditional lensometers comprise an instrument used to determine the power and astigmatism (sphere and cylinder) of a spectacle lens. In particular, traditional lensometers comprise a centered telescopic optical system that includes a reticule and neutralizing lenses that can be employed to measure sphere and cylinder power as well as axis. A dial called the power drum is used in conjunction with an axis dial for introducing test correction such that lines in the reticule appear straight and in focus to the operator. Newer lensometer systems are automatic, however, these instruments still rely on the principle of neutralizing sphere and cylinder utilizing movable lenses.

Such conventional systems and techniques work adequately for lenses measuring sphere and cylinder. The measurement of sphere and cylinder of the spectacle lenses enables optometrists and ophthalmologists to provide conjugate correction for a near-sighted or a far-sighted patient who possibly has astigmatism as well. However, corrective optics provided on the basis of these sphere and cylinder measurements are often not suitable for correcting a person's vision. What is needed are improved systems and methods for measuring refraction of patients and for providing appropriate vision correction.

SUMMARY OF THE INVENTION

One embodiment of the invention comprises a lensometer for measuring waveshaping properties of a corrective lens across at least a portion of the corrective lens. This lensometer comprises a light source for emitting light, beam-tailoring optics, and a Talbot plane self-imaging wavefront sensor. The beam-tailoring optics receives light from the light source and outputs a light beam having a beam size at least as large as the portion of the corrective lens to be measured. The light source, the beam-tailoring optics, and the corrective lens are disposed along an optical path such that the light beam propagates through the corrective lens. The Talbot plane self-imaging wavefront sensor is disposed in the optical path to receive the light beam after the beam has passed through the corrective lens. The Talbot plane self-imaging wavefront sensor is configured for use in determining the waveshaping properties of the corrective lens.

Another embodiment of the invention comprises a method of measuring waveshaping properties of a corrective lens across at least a portion of the corrective lens. In this method, a beam is propagated through the corrective lens. The beam, having passed through the corrective lens, is propagated through at least one two-dimensional modulation pattern thereby producing a near field diffraction pattern at a Talbot plane. The near field diffraction pattern is imaged at the Talbot plane and a measure of the waveshaping properties of the corrective lens is determined based at least in part on the near field diffraction pattern.

Another embodiment of the invention comprises a combination lensometer/ocular measurement system for measuring refractive properties of an object under test selected from the group comprising a corrective lens and an eye. The measurement system comprises a light source, beam-tailoring optics, support structure, and a wavefront sensor. The light source emits a beam of light along a first optical path to the object under test. The beam-tailoring optics alters one or more characteristics of the beam based on whether the object under test comprises a corrective lens or an eye. The support structure positions the object under test in the beam for measurement and the wavefront sensor is disposed to receive light from the object under test for measurement of optical wavefronts received therefrom.

Another embodiment of the invention comprises a method of measuring waveshaping properties of a wavefront. In this method the wavefront is propagated through at least one two-dimensional modulation pattern thereby producing a self-image at a self-image plane of the two-dimensional modulation pattern. An image of the self-image plane is formed. Contributions from portions of the image of the self-image plane are reduced based on comparisons of a characteristic of the portions of the image with a threshold and a measure of the wavefront is determined based at least in part on the image of the self-image plane.

BRIEF DESCRIPTION OF THE DRAWINGS

The details of the various preferred embodiments, both as to their structure and operation, can best be understood in reference to the accompanying drawings, in which like reference numerals refer to like parts, and in which.

DETAILED DESCRIPTION OF EMBODIMENTS OF THE INVENTION

Figure 1:
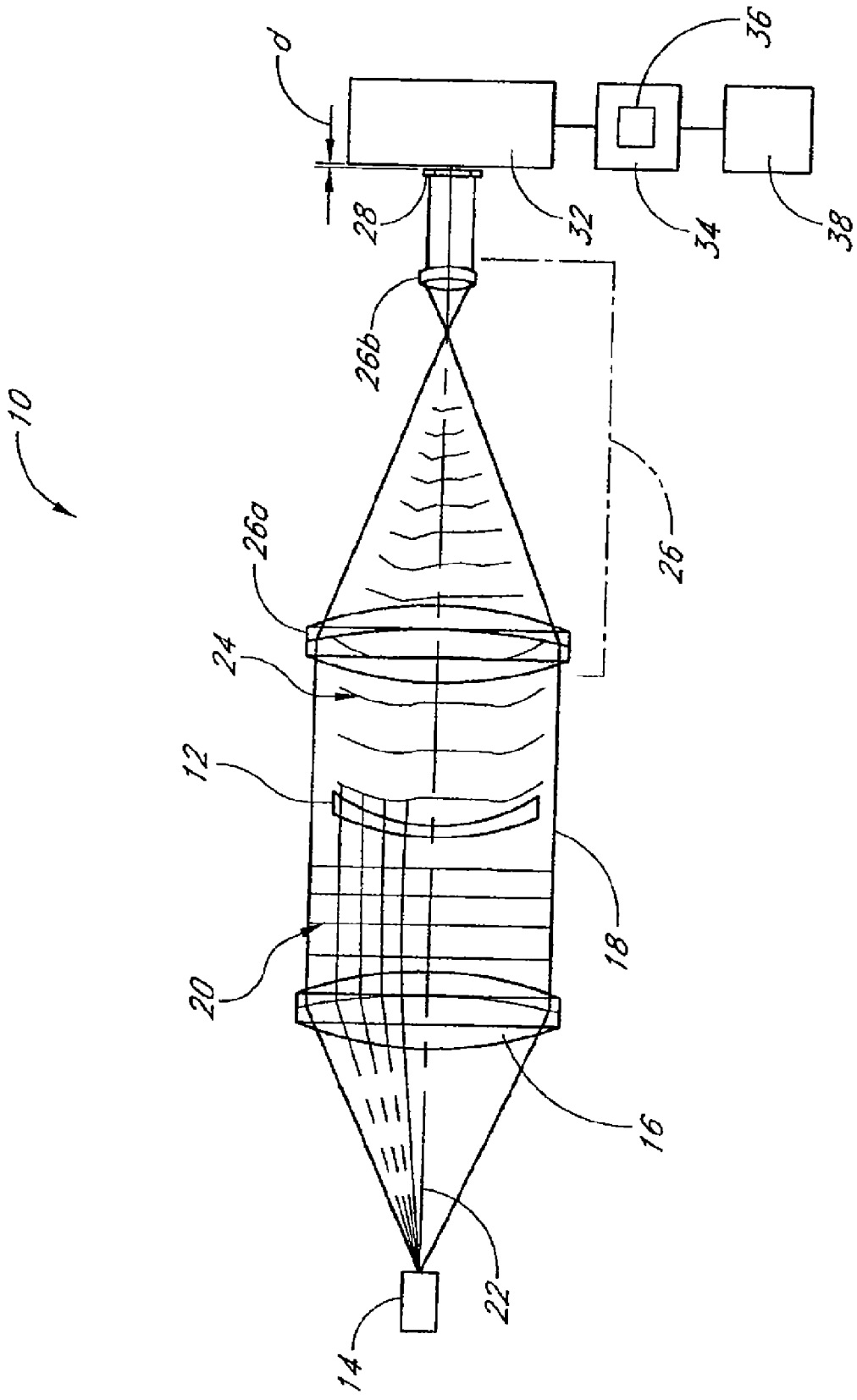
FIG. 1 is a schematic diagram of a system for measuring and characterizing refractive properties in an optical lens such as, for example, a spectacle lens or a contact lens.

FIG. 1 depicts a lensometer 10, which is an optical system for measuring refractive or wave-shaping properties of a test lens 12. The lensometer 10 comprises a light source 14 such as a laser diode. The laser diode light source 14 preferably outputs light at a wavelength of about 550 nanometers (nm) although other wavelengths including infrared wavelengths may be employed to illuminate the test lens 12. Moreover, the laser preferably outputs a beam of light. The light is preferably substantially collimated, for example, preferably at less than about 30 arc seconds. Other types of lasers and light sources may be used for this purpose. In various preferred embodiments, the light source is semi-coherent.

The lensometer 10 further comprises beam tailoring optics, e.g., beam expanding and collimating optics 16 in the embodiment in FIG. 1. The beam expanding and collimating optics 16 may comprise one or more lenses or other optical elements configured to collect light emitted from the light source 14 and produce a beam 18 comprising substantially planar wavefronts 20. In the case where the beam output by the laser is already substantially collimated, an afocal system that expands the size of the beam and produces another larger collimated beam may be employed. In some embodiments, the beam expanding optics 16 may further comprise an element such as, for example, a pin hole aperture or spatial filter, lens, or other optical element, for causing the light output from the laser diode to diverge. In other cases, the light source 14 may provide a sufficiently divergent beam. For example, many laser diodes have substantially divergent beams. To collimate the divergent beam, the beam expanding and collimating optics 16 may have a focal length and a position with respect to the light source 14 or pin hole aperture such that light output from the light source 14 is substantially collimated by the beam expanding and collimating optics. The beam expanding and collimating optics 16 is shown in FIG. 1 converting waves in a divergent beam emitted from the laser diode light source 14 into substantially planar waves 20. However, in other embodiments, the waves incident on the lens under test 12 need not be plane waves. For example, in the case where null optics is employed, as discussed below, the waves incident on the lens under test 12 may be other than planar. Similarly, in some embodiments, beam expanding optics 16 may be employed to yield a beam that is not a substantially collimated.

As shown in FIG. 1, the waves produced by the beam expanding optics 16 preferably have a size (e.g., diameter) that is substantially large with respect to, and possibly larger, than the lens 12 to be measured. Accordingly, in certain preferred embodiments, the beam expanding and collimating optics 16 has a size sufficiently large to provide illumination over a substantial portion of the test lens 12. The beam 18 may, for example, illuminate at least about 50% of the lens area. In certain preferred embodiments, 70%, 80%, or 90% of the lens area is illuminated. In some embodiments, the beam 18 may substantially illuminate the portion of the spectacle or contact lens that is utilized by the wearer. Accordingly, the beam 18 need not in every case be as large as the test lens 12, but preferably is sufficiently large to probe the portion of the lens through which light is collected during use to form an image on the retina of the wear's eye. Producing an oversized beam 18 such as shown in FIG. 1, however, may be preferred as well. An oversized beam 18 may advantageously increase tolerances in positioning the lens under test 12 and in accommodating different shapes and size lenses.

Spectacles may range between about 45 and 65 mm in width and about 25 and 45 mm in height or up to 65 mm in diameter in some cases. In the case where the test lens 12 comprises spectacles, preferably the beam 18 produced by the beam expanding optics 16 that is passed through the test lens is between about 65 and 75 mm at the test lens. Accordingly, the beam expander and collimating optics 16 preferably also has a suitably large pupil. The aperture size or exit pupil of the beam expander and collimating 16 may, for example, have diameter between about 65 and 75 mm. In embodiments where the aperture or exit pupil are not circularly symmetric, the size may be characterized by a width of between about 45 and 65 mm and a height of between about 20 and 65 mm. Sizes outside these ranges, however, may be employed.

In the case where the test piece 12 comprises a lens blank, a larger beam may be preferred. In such cases, the aperture size or exit pupil of the beam expander and collimating optics 16 may for example have diameter between about 20 and 75 mm. In the case where the test piece 12 comprises a contact lens, a smaller beam may be preferred. In such cases, the aperture size or exit pupil of the beam expander and collimating optics 16 may for example have diameter between about 10 and 15 mm. Sizes outside these ranges, however, are also possible.

As illustrated in FIG. 1, the light source 14, beam expanding/collimating optics 16, and test piece 12 are preferably aligned along an optical axis 22 herein designated the z-axis, with orthogonal x and y axes extending therefrom. Light output from the light source 14 propagates along an optical path following the optical axis 22 through the beam expander and collimating optics 16. The test piece 12 is inserted in the optical path. Depending on the shape and refractive properties of the test lens 12, the waves of light propagating through the test lens will be altered as shown in FIG. 1 wherein the plane waves 20 passing through the lens under test are transformed into aberrated waves 24.

In the lensometer 10 shown in FIG. 1, the optical system 10 further comprises beam reducing optics 26 comprising at least one lens or optical element disposed along the optical axis 22. The beam reducing optics 26 in FIG. 1 is an afocal beam reducing relay comprising first and second optical elements 26a, 26b. These optical elements 26a, 26b have respective focal lengths and are disposed longitudinally with respect to each other to reduce the size of the beam. For example, the first optical element 26a may have a large focal length and the second optical element 26b may have a small focal length. The rear focal point of the first optical element 26a may be substantially coincident with the front focal point of the second optical element 26b to produce an afocal system. The beam reducing optics 26 may, for example, comprises a 10:1 reducer having respective focal lengths of a ratio of 10:1. The amount of reduction may be more or less in other embodiments. For example, the range of reduction may be from about 20:1 to 2:1 in certain embodiments but should not be restricted to this particular range.

The beam reducing optics 26 preferably has a sufficiently large size to accommodate the beam 18 directed through the lens under test 12. In the case where the test lens 12 comprises spectacles, which may range between about 45 and 65 mm in width and about 25 and 45 mm in height or up to 65 mm in diameter in some cases, preferably the beam reducing optics 26 also has a suitably large pupil. The aperture size or entrance pupil of the beam reducing optics 26 may, for example, have diameter between about 60 and 80 mm. In embodiments where the aperture or entrance pupil are not circularly symmetric, the size may be characterized by a width of between about 70 and 90 mm and a height of between about 35 and 55 mm. Sizes outside these ranges may be employed in other embodiments.

In the case where the test piece 12 comprises a lens blank, the aperture size or entrance pupil of the beam reducing optics 26 may for example have diameter between about 70 and 100 mm. In the case where the test piece 12 comprises a contact lens, the aperture size or entrance pupil of the beam reducing optics 26 may for example have diameter between about 10 and 15 mm. Sizes outside these ranges are also possible.

In certain embodiments, the afocal beam reducing optics 26 shown in FIG. 1 may be replaced with a non-afocal system. Similarly, the beam output from the beam reducing optics 26 need not be a substantially collimated beam although a substantially collimated beam is preferred.

The lensometer 10 further comprises at least one periodic diffractive element or two-dimensional modulation patterned element 28 disposed along the optical axis 22 and positioned to receive the light from the reducing optics 26. This periodic diffractive element or modulation pattern or element 28 may comprise, for example, a fine-pitch two-dimensional pattern with periodic features in the x and y directions such as a checkered board pattern or grid-like pattern. The diffractive element 28 may also comprise without limitation, a ruled two-dimensional diffraction grating, screen, grid, holographically generated transmission or reflective gratings, or the like. Alternative types of elements are also possible. Additionally, this periodic diffractive element 28 may have substantially same or different period in different, e.g., orthogonal x and y directions. One or more patterns may be employed. For example, two gratings with same or different periodicity in different directions may be superimposed to produce a pattern that is periodic in two directions. Other designs are possible as well.

The periodic diffractive element 28 is preferably disposed at or in proximity to a location in the optical system 10 where the test piece 12 is re-imaged. More particularly, this location preferably corresponds to a re-imaged pupil of the lens under test 12. The periodic diffractive element pattern 28 may, however, be disposed a distance from these locations although performance may be reduced.

As shown in FIG. 1, the light beam propagates along the optical path and through the periodic diffractive element 28. The element 28 with periodic features modulates a wavefront from the beam of light passed through the lens under test 12. The modulated wavefront propagates a minute distance, d, e.g., few millimeters, beyond the periodic diffractive element 28, where an image of the periodic diffractive element re-images as a result of the Talbot effect. According to the Talbot effect, when certain periodic intensity modulation patterns are placed at the optical pupil of the system (e.g., lens or eye), the modulation pattern will reappear at predictable longitudinal positions along the propagation path. These positions are spaced apart from the diffractive element 20 by integer multiples of the distance, d. These predictable longitudinal positions are referred to herein as Talbot planes.

A light sensor 32 such as but not limited to a CCD, CMOS, or other detector array or camera may image any of the planes that correspond to the Talbot or "self-imaging" planes a distance n×d from the periodic diffractive element 28, where n is an integer. The self-imaging distance, "d," is dependent on the spectral wavelength of the wavefront and the spatial frequency of the periodic diffractive element pattern. In some embodiments, a sensor plane of a sensor array is disposed at one of the self-imaging planes. Alternatively, the optical system 10 may comprise a camera having a lens that relays the self-image plane onto a detector located a distance away. Preferably, the sensor is located so as to image a region the self-imaging plane or within about 1% of the distance, d, from the self-image plane.

If the periodic diffractive element 28 is placed where an image of the lens under test 12 is formed, the lens under test together with the periodic diffractive element pattern are "self-imaged." Likewise, the detector 32 will record the modulation pattern together with the test lens 12. If the lens under test 12 contains wavefront aberrations, the modulation pattern will be distorted relative to the periodic modulation element. The distortions on the periodic "carrier" intensity pattern can be extracted through computer algorithms applied to the recorded intensity values determined by the detector 32.

In various preferred embodiments, a signal from the detector 32 is sent to a data processor (i.e., computer) 34 for processing. The signal processor extracts from the signal, information about the phase of the wavefront after propagating through the lens under test 12 and the periodic diffractive element 28. Information regarding the wave-shaping properties of the test lens 12 is thereby obtained from the signal. To perform such processing, the processor 34 preferably accesses a software-implemented module 36 and outputs a signal representative of the phase of the wavefront to an output device 38. The output device 38 may comprise, but is not limited to a monitor, display, printer, computer, network, or other appropriate device.

By utilizing the various techniques described herein, a mathematical representation of the wavefront and of the aberrations of the wavefront having passed through the test piece 12 can be obtained. The wave-shaping properties, e.g., refractive properties and/or shape of the lens 12 may thereby be obtained. Similarly, the aberrations of the lens 12 including the higher order terms (e.g., $3^{rd}$ order aberrations and higher) may be quantified.

Corrective lenses such as contacts and spectacles may therefore be characterized more precisely. The optical parameters of the lens 12 may be recorded or used to provide appropriate corrective optics for patients. The measurements of the lens under test 12 may assist in fabrication of the lens and may be integrated with the manufacturing process, e.g., for quality control. In certain embodiments, for example, the measurement may be employed to monitor the progress of the shaping of the lens and may be employed in a process of repeated measurement and refinement wherein the corrective lens is shaped based on measured waveshaping properties. This process may be iterative. In such embodiments, additional shaping, fabrication or other correction can be under-taken based on the measurements to obtain the desired lens parameters. The apparatus and techniques may similarly be applied to lens blanks during the fabrication stage and provide guidance regarding fabrication of the lens blank.

Figure 2:
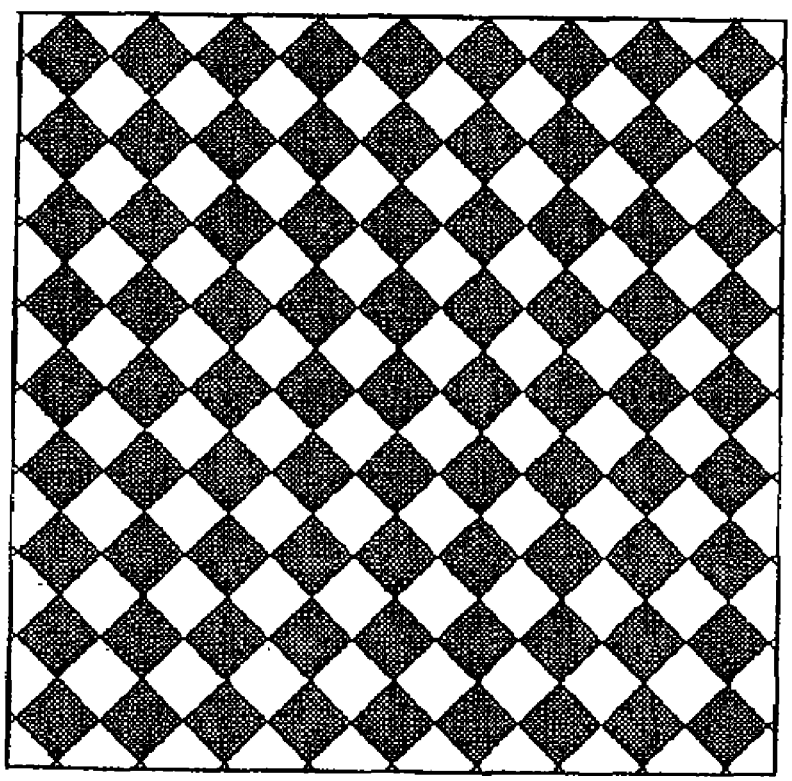
FIG. 2 is a front view of a checkered periodic diffractive element pattern used in the system of FIG. 1.

To provide improved results, a checkerboard pattern such as shown in FIG. 2 may be used in the lensometer system 10. This checkered board pattern is oriented at angles of +45 and −45 degrees with respect to the sides of the periodic diffractive element 28. Preferably, the pattern 28 comprises a plurality of periodic features. In various preferred embodiments, this pattern 28 is a transmissive element. Preferably, the periodic features modulate the light that is received by the pattern resulting in an output from the pattern that has a modulated intensity.

The periodicity of the pattern 28 may be on the order of about 20 to 120 microns although values outside these ranges are possible. Similarly, the checkered board pattern may comprise dark and light (e.g., transmissive and opaque or reflective and non-reflection regions) each between about 10 and 60 microns in size. The width of the patterned light blocking portions is preferably the same as the openings in the patterned element. The size, configuration and arrangement of the features in the pattern, however, may be different. The pattern 28 may, for example, include more or less features in different embodiments.

Figure 3:
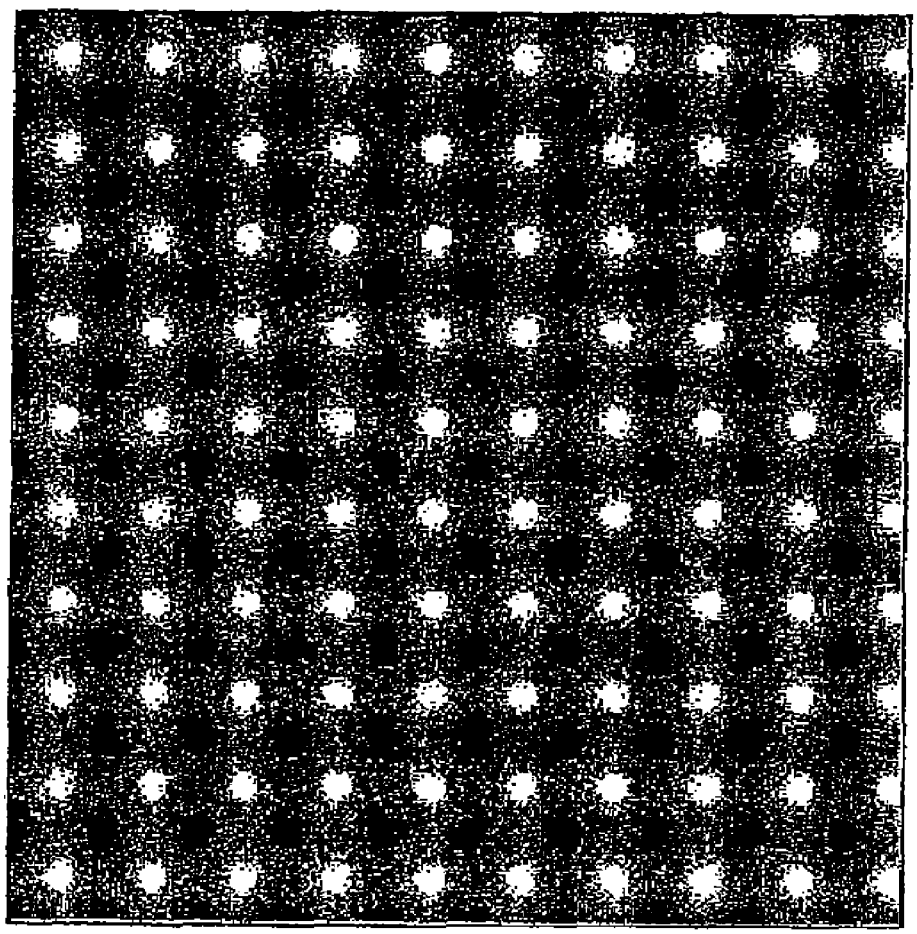
FIG. 3 is a front view of a two-dimensional sinusoidal periodic diffractive element pattern.

The checkerboard pattern approximates a two-dimension sinusoidal pattern 84 such as shown in FIG. 3 and which also may be employed. The corresponding transmission function, $\tau_I(x,y)$, for the grayscale two-dimensional sinusoidal optical modulation pattern 84 shown in FIG. 3 is described by the following equation:

$$\tau_I(x, y) = \frac{1}{2}\left(1 + \frac{1}{2}\cos\left(\frac{2\pi x}{P}\right) + \frac{1}{2}\cos\left(\frac{2\pi y}{P}\right)\right) \quad (1)$$

where x and y are coordinates defining position across the pattern and P corresponds to the period of the sinusoidal modulation.

The sinusoidal intensity modulation element 28 produces a sinusoidal Talbot image. The carrier signal referred to above is thus sinusoidal in this case. Aberration in the wavefront manifests itself as modulation of this sinusoidal carrier. By using a sinusoidal carrier, the aberration information can be extracted more accurately, e.g., through Fourier transformation, with reduced or substantially no loss of information caused by high-order interference between the diffraction pattern of the periodic diffractive element 28 and the high-order aberrations of the wavefront. "Ringing" caused by sharp edges of non-sinusoidal intensity patterns that may result from non-smoothly varying periodic diffraction patterns can thereby be reduced or eliminated. Accordingly, the high-order information does not "diffract away" into high-order lobes. In principle, the sinusoidal optical element should enable measurement of extremely high-order aberration information.

Conventional technologies used to manufacture transmission gratings, however, may not be ideal for creating grayscale transmission functions. Binary patterns comprising a pair of discrete transmission levels may be more easily fabricated. In such binary patterns, the transmission of a given discrete spatial area is selected to be either a high value ("1") corresponding to high transmission, e.g., about unity, or a low value ("0") corresponding to low transmission, e.g. at or near zero. In various embodiments, a binary transmission function may comprise a plurality of discrete areas or "pixels" arranged in a desired pattern to resemble a continuous pattern. To arrive at an appropriate binary pattern that approximates, for example, a continuous two-dimensional sinusoidal function, a threshold transmission value may be selected. Values above the threshold are designated as high values ("1") and rounded up to about unity transmission whereas transmission values below the threshold are designated as low values and rounded down, e.g., to about zero ("0"). Such threshold approximations applied to the continuous two-dimensional sinusoidal transmission function yield the rotated checkerboard pattern 86 comprising a lattice of diamond shapes as shown in FIG. 2. The transmission, $\tau_B(x,y)$, of such a two-dimensional pattern 86 may, for example, be described by the following equation:

$$\tau_B(x, y) = \text{round}\left(\frac{1}{2}\left(1 + \frac{1}{2}\cos\left(\frac{2\pi x}{P}\right) + \frac{1}{2}\cos\left(\frac{2\pi y}{P}\right)\right)\right) \quad (2)$$

where x and y are coordinates defining position across the pattern and P corresponds to the period of the sinusoidal modulation.

The checkered board pattern 86 advantageously closely resembles and approximates the continuous two-dimensional sinusoidal function. Computer modeling of the propagation of an aberration-free wavefront through continuous and binary periodic patterns confirms that residual phase error is reduced with these periodic diffractive element patterns. Examination of the Fourier transforms of both checkerboard and sinusoidal periodic elements exhibit reduced or minimize error in the vicinity of the fundamental frequency of the periodic pattern. Moreover, the residual phase error at the Talbot plane for the binary checkerboard diffractive element substantially matches that of the continuous two-dimensional sinusoidal diffractive element. The spatial frequency spectrum is thus preserved in the vicinity of the fundamental spatial frequency of the idealized sinusoidal periodic pattern. The spectrum in the vicinity of the fundamental frequency is not corrupted by harmonic components of the binary periodic element. A realizable and accurate approximation to a continuous sinusoidal element may therefore be fabricated using inexpensive manufacturing techniques.

In one embodiment, the checkerboard periodic diffractive element similar to that shown in FIG. 2 comprises thin glass plate such as BK7 glass having clear diamond portions and opaque diamond portions formed by black chrome that is deposited on a front side and photo-etched. The checkerboard pattern may be oriented at +45° and −45° with respect to the sides of the optical element 28. The periodicity in one example is about 56 microns with a given transmissive or opaque diamond being about 28 microns along a side. The periodic diffractive element 28 is square and about 14.22 millimeters by 14.22 millimeters with a thickness of about 1.56 millimeters. A backside of the glass element may be coated with a bandpass filter, e.g., centered at about 830 nanometers and AR coated for reduced reflection at the nominal wavelength of the excitation beam. Other designs, however, are possible.

Figure 4:
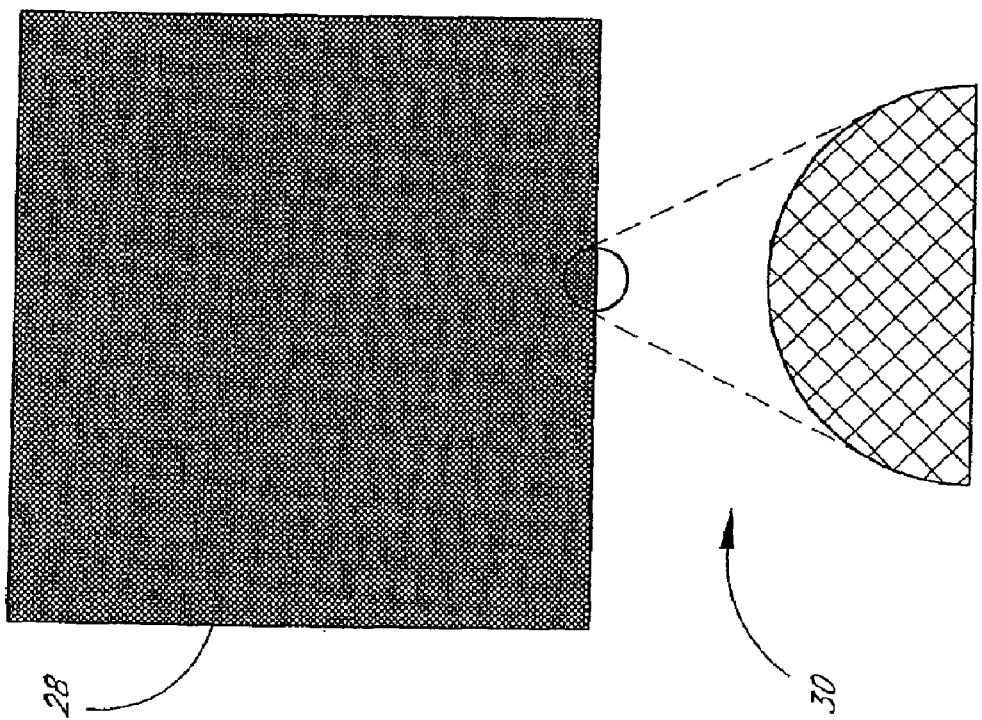
FIG. 4 is a front view of another embodiment of a periodic diffractive element that may be used in the system of FIG. 1.

Another exemplary periodic diffractive element pattern 28 that may be employed is shown in FIG. 4, which includes an expanded view 30 of a portion of the pattern. Light incident on the pattern passes through an array of openings in the element 28. The periodic diffractive element 28 may comprise, for example, a first plurality of substantially opaque linear features periodically arranged and spaced apart along one direction (e.g., x direction) and a second plurality of substantially opaque linear features periodically arranged and spaced apart along an orthogonal direction. The first plurality and the second plurality of periodic, spaced apart, linear features, being orthogonal, create an array of openings with periodicity in two dimensions. Light incident on the element may pass through this two-dimensional array of openings, while a portion of the light is blocked by the substantially opaque linear features, thereby modulating the intensity of the light.

The periodicity of the pattern 28 may be on the order of about 20 to 120 microns although values outside these ranges are possible. Similarly, the pattern may comprise openings between about 10 and 60 microns in size separated by opaque lines between 10 and 60 microns wide. The width of the patterned light blocking portions is preferably the same as the openings in the patterned element.

Other types of gratings or periodic elements 28 may also be used. In other embodiments, for example, the element 28 need not be transmissive and may instead be reflective. The configuration of the lens measurement system 10 may likewise be different. In certain embodiments, a suitably constructed phase modulation element could be used to produce the desired intensity modulation. The phase modulation element may have variable path length that varies sinusoidally in two orthogonal directions. The periodic diffractive element 28 may also be formed differently and the pattern may be different as well. More than two may be used at various orientations with respect to each other. The pattern need not be linear. The periodic diffractive element 28 may, for example, comprise at least partially curved rulings. Similarly, the apertures in the periodic diffractive element 28 need not be square or diamond shaped but may comprise other shapes including but not limited to circles, ellipses, etc., as well as rectilinear shapes such as, e.g., triangles, hexagons, pentagons, etc. The pattern need not be completely periodic or regular. Other embodiments are possible. Other methods of manufacturing sinusoidal or non-sinusoidal patterns that may or may not approximate a continuous two-dimensional sinusoidal pattern may be used.

Other types of system configurations can be employed as well. In one exemplary embodiment shown in FIG. 5, null optics 88 are used to control the beam 18 in the lensometer 10 and to increase the dynamic range of the wavefront measurements. The optical system 10 may include a null lens 90 supported by a lens holder 92, for example, between the beam expanding and collimation optics 16 and the lens under test 12. The lens holder 92 positions the null lens 90 along the optical axis 22 and in the optical path of the beam 18. The null optics 88 and lens holder 92 can be placed before or after the lens 12 to be tested. In various preferred embodiments, the null optics 88 has an optical power that is substantially conjugate to the optical power in the test lens 12. Accordingly, the combination of the null optics 88 and the lens under test 12 does not substantially alter the beam and disrupt operation of the lensometer 10 or hinder accurate measurement. If for example, the lens under test 12 has too much or too little optical power, the optical beam 18 may be caused to excessively converge or diverge. In such cases, the null lens 90 is preferably selected to offset the optical power of the test lens 12, for example, to maintain a substantially collimated beam output from the lens under test and to reduce the diameter of the optics such as beam reducing element 26*a*, the input to the relay lens system. Measurements of the aberration at the optical sensor 32 will thereby be combined with refractive properties of the null lens 90, which are preferably accurately known possibly by independent measurements using the Talbot-based lensometer. In this case, the aberration in the test lens 12 is the sum of the contributions from the null lens 90 and the aberration measured at the sensor. As a result, higher levels of aberration in the test lens 12 can be measured. Increased dynamic range is thereby achieved. Null optics may be employed in other ways as well.

In various embodiments, the lens holder 92 is configured such that the null lens 90 can be switched out and replaced with another null lens to alter the optical power of the null optics 88. For example, the lens holder 92 may comprise a wheel with a plurality of lenses mounted thereto and that is rotatable such that different of the lenses may be rotated into or out of the optical path of the beam 18. This wheel may be motorized or otherwise automatically driven or may be manually operated. One or more such wheels can be employed in series such that combinations of lenses may be inserted into the optical path of the beam to vary the optical power and aberrations. Also, although the null optics 88 is shown disposed in the optical path between the light source 14 and the test lens 12, the null optics may be positioned elsewhere, such as between the test lens and the first lens of the relay system 26. Also, other techniques can be used to alter the null optics 88. For example, the longitudinal position of one or more null lenses 90 along the optical path can be varied to alter the resultant optical power of the null optics 88. Other types of optical elements, beside null lenses may be employed as well. Preferably, however, the null optics 88 may be varied to vary the optical power so as to at least partially offset the optical power and/or aberration in the test lens 12.

Figure 5:
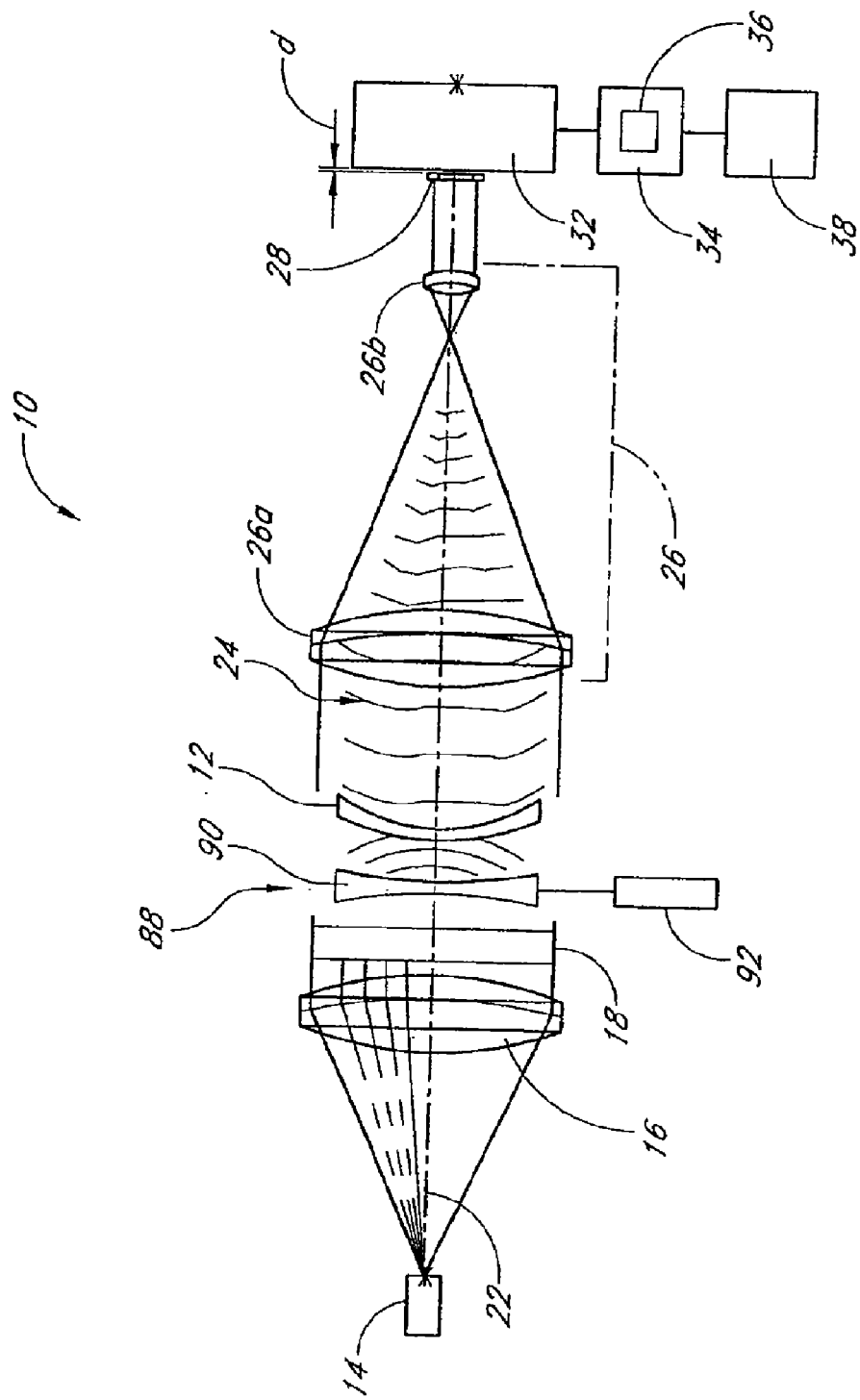
FIG. 5 is a schematic diagram of a system for measuring and characterizing refractive properties in a lens comprising a null lens.

As described above, other variations in the configuration of the lensometer 10 as well as the arrangement and type of optical components included therein may be used. In certain embodiments, for example, beam reduction optics 26 do not produce a collimated beam incident on the periodic diffractive element 28. Such a configuration is shown in FIG. 5. The reducing optics 26 may, for example, comprise a non-afocal system such that the collimated beam received by the reducing optics is not output from the reducing optics 26 as a collimated beam. Although the beam is reduced at the element 28, the beam is not collimated at that location. Other variations of the beam reducing optics 26 and other portions of the lensometer 10 and methods of operation are possible. For example, the beam reducing optics 26 may or may not comprise a relay and may comprise a single imaging lens in some embodiments.

The lensometer 14 preferably produces very high spatial resolution, with certain embodiments having greater than about 300×300 measurement points for the portion of the test lens 12 being evaluated. The lensometer instrument 10 preferably offers enough resolution to measure relatively sharp phase errors and can accurately characterize higher order, high spatial frequency, aberrations and wavefront errors. A given wavefront may be described in terms of polynomials such as Zernike polynomials, each polynomial being of some order, n, with high order aberrations corresponding to polynomials of order three and higher. The wavefront may also be described in other manners know to those familiar in the art.

The Talbot or self-imaging based wavefront sensor described herein is superior to Shack-Hartmann interferometers, which use a lenslet array such as a 9×9 lenslet array. These Shack-Hartmann interferometers, which are conceptually based on geometric optics, have significantly reduced resolution and dynamic range that limit their ability to handle complex waveform shapes. For example, lenslet arrays used in conventional Shack-Hartmann interferometers have less than about 100 lenslets and correspondingly sample the wavefront at less than about 100 locations. In contrast, the periodic diffractive element 28 in the Talbot/self-imaging plane wavefront sensors described above may have about 10,000 apertures and thus sample the wavefront at about 10,000 locations, thereby increasing the resolution of the self-imaging system 10. Additionally, Shack-Hartmann interferometers exhibit limited linearity and have sub-aperture alignment issues. Scaling to large numbers of sub-apertures to measure high-order aberrations is also complex.

The lensometer 10 described herein offers other advantages as well. For example, measurements with the self-imaging based lensometer 10 are relatively fast. A sequence of short exposures can be quickly obtained with only one initial alignment. The captured images are preferably pre-screened for artifacts and processed. The results may be ready to display in less than one minute.

After the wavefront data is obtained and analyzed, the wavefront analysis results can be displayed on a screen or display for the user to view. The results can also be encoded into barcode format or transferred electronically such as through the internet. The Zernike data and other lens specifications may, for example, be encoded in a barcode on a label for the test piece. In some cases, this information may be sent to a lab for additional processing of the lens. In other exemplary embodiments, the lensometer 10 may be connected to an office practice management system via wireless network, intranet, internet, or ethernet. This office practice management system may include one or more computers or microprocessors. The office practice management system may also include storage or memory for recording measurements and patient data. The office practice management system may be linked with insurance providers, other healthcare providers, lens and eyewear manufacture or sales facilities, etc., and accordingly information may be conveniently communicated to such destinations.

Figure 6:
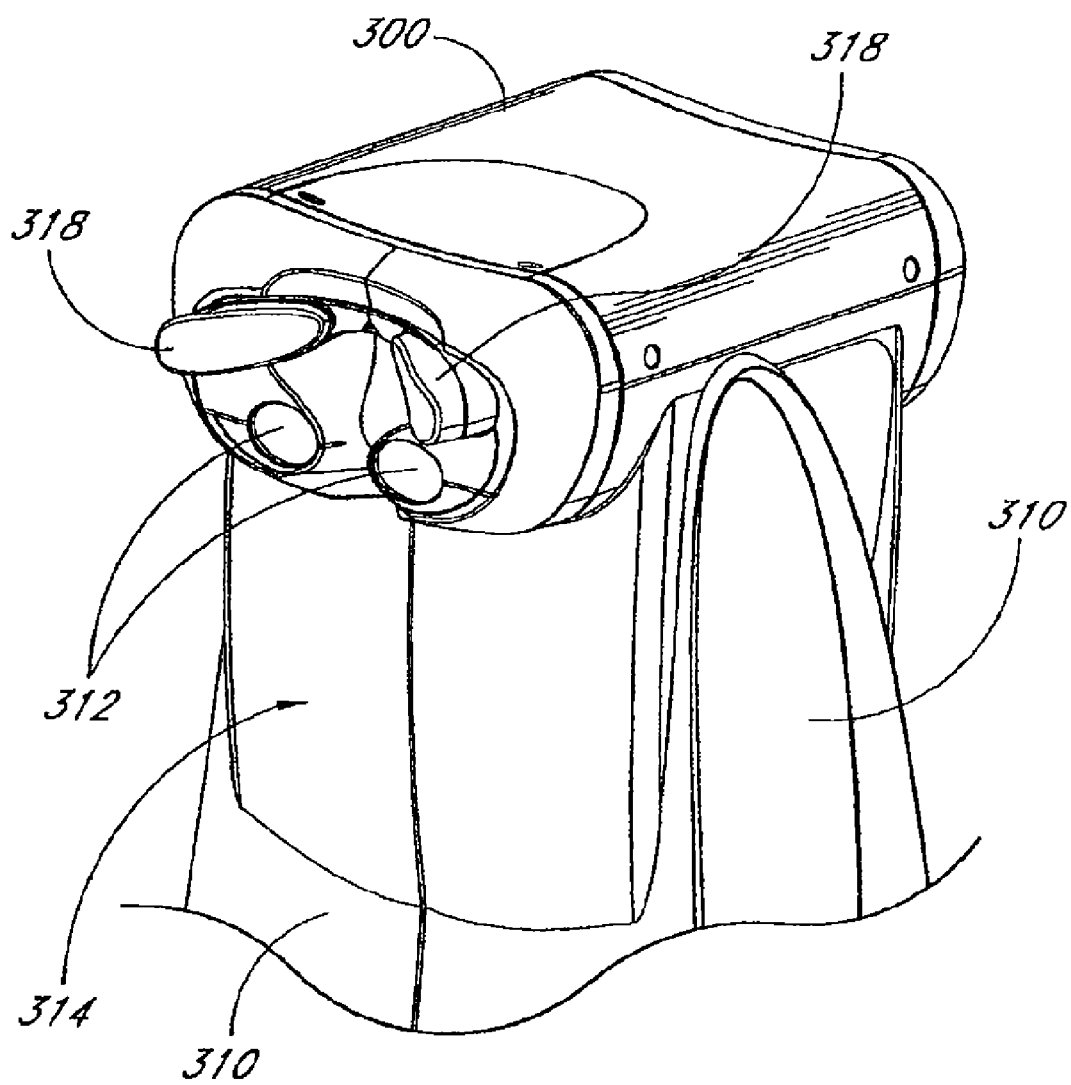
FIG. 6 is a partial perspective view of an instrument that can be configured to measure refractive properties of a person's eyes as well as to measure spectacle lenses.

In various embodiments, an instrument may be configured to operate as an ophthalmic instrument for measuring the refractive properties of the eye and also as a lensometer for measuring spectacle lenses and/or contact lenses. The instrument may operate in either of the two modes. Combining the lensometer function with the measurement of refractive properties of the eye offers powerful capabilities to the eyecare professional. A perspective view of a binocular instrument 306 that is both a lensometer and an ocular measurement system is shown in FIG. 6. The instrument 300 may comprise a housing 310 that surrounds and protects optics contained therein and supported on a frame (not shown).

To perform the ocular measurements, the patient looks into a pair of oculars or eye pieces 312 on a front face 314 of the instrument housing 310. The instrument 300 may include forehead rests 318 for comfortable positioning of the eyes with respect to the oculars 312. When performing precise wavefront measurements of the eye, the subject's eye is preferably focused and in a natural, comfortable state, thereby reducing or minimizing errors due to accommodation or eye movement. One method of ensuring that the subject is comfortable and relaxed is to present an image to the eye which allows the subject to fixate on a specific item. When viewing this image, the subject's vision is preferably corrected to a level allowing the person to fixate on the object. For example, the subject is preferably measured while viewing a natural scene at the desired distance for which the prescription will be generated. For an eye exam, the patient may view an eye chart or scene image placed at about 16 feet or greater from the subject. The ophthalmic diagnostic system 300 therefore preferably provides correction, such as spherical and astigmatic correction, through a lens to a real object at about 16 feet away. However, providing a 16 foot distance may pose a problem for some exam areas due to space constraints. This system 300 therefore preferably also provides a mode directing the subject's vision to an internal fixation target, if needed, for use in small rooms where, e.g., a 16 foot distance to a target, cannot be accommodated. An image formed at a distance of about 16 feet may be used as a target. Accordingly, various preferred embodiments include an internal/external fixation target design.

Figure 7:
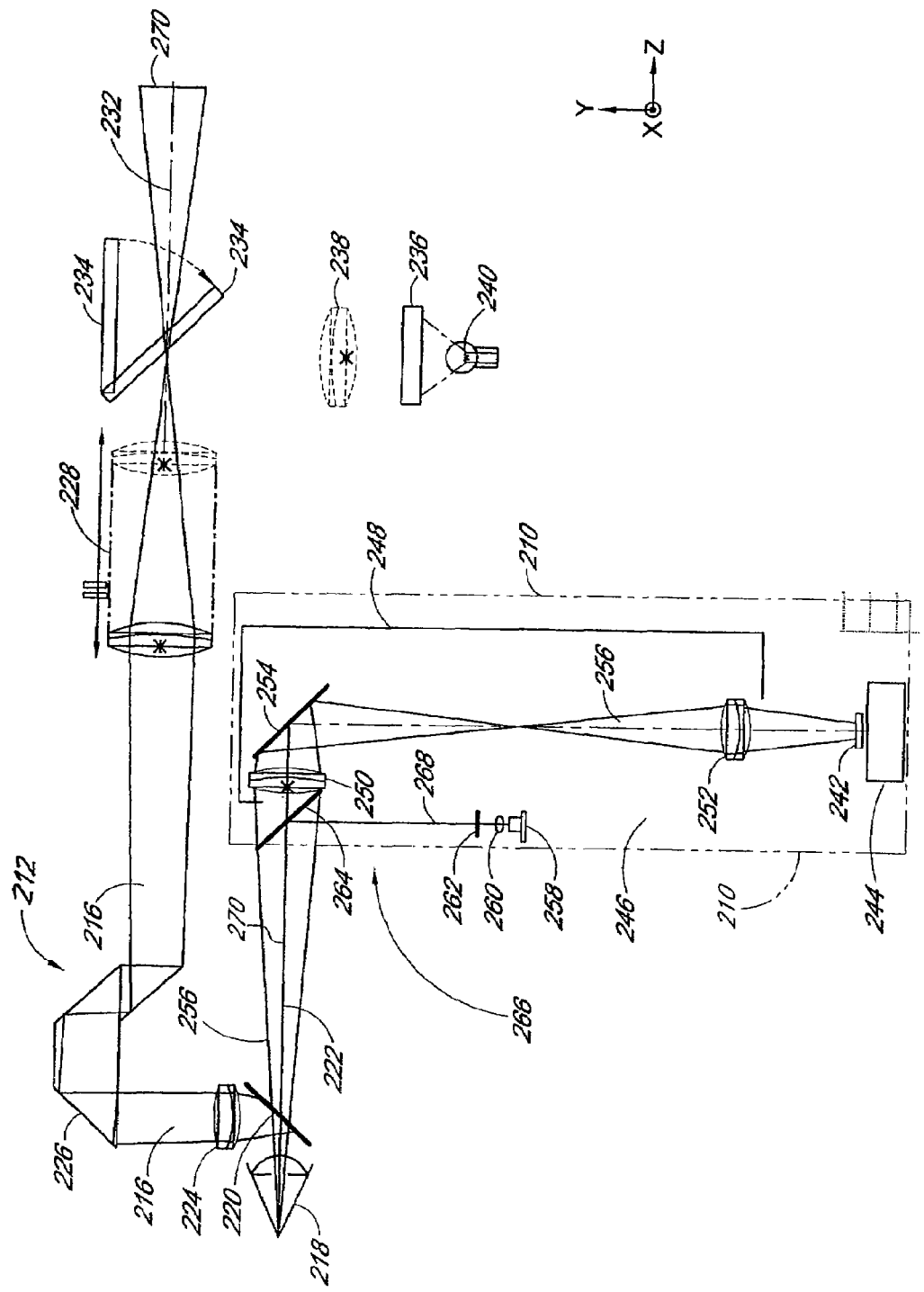
FIG. 7 is a schematic diagram of the optical instrument of FIG. 6 configured as an ocular measurement system for characterizing the refractive properties of an eye.

FIG. 7 schematically illustrates an exemplary optical design that may be employed. As shown in FIG. 7, the instrument 300 comprises a wavefront sensor 210 and visual optics 212 through which the patient views internal or external targets. Accordingly, the visual optics 212 comprises optical elements for visible light. Various embodiments of the invention comprise binocular wavefront aberrometers as refractions taken under binocular conditions are preferred as being generally more accurate than those taken under monocular conditions. Accordingly, the visual optics 212 includes two optical paths 216, one for each eye 218. The pair of optical paths 216 are preferably parallel although are not required to be so. In the schematic view presented in FIG. 7, only one of these two paths 216 are shown. The two paths 216 for the two eyes, however, are similar in a binocular system.

As shown in FIG. 7, the visual optics 212 includes an infrared (IR)/Visible beamsplitter 220 placed directly in front of the eye 218. In this exemplary design, this beamsplitter 220 has a surface oriented at an angle of about 45° with respect to an optical axis 222 through the beamsplitter. The beamsplitter 220 has a reflective surface that is situated along the respective optical path 216 and preferably reflects visible light. The reflective surface, however, is preferably transparent to certain IR wavelengths used in the instrument 300.

The visual optics 212 further comprises a fixed lens 224, an inverting prism 226, and a movable lens 228 in this optical path 216. The inverting prism 226 comprises a plurality of reflective surfaces arranged to invert and flip an image (e.g., rotate the image about orthogonal x- and y-axes in a plane perpendicular to an optical axis 232 through the visual optics path 216). The optical elements are arranged along the optical path 216 such that visible light from the internal or external target passes through the movable lens 228, the inverting prism 226, and the initial lens 224 and is reflected off the beamsplitter 220 and into the eye 218.

The prism 226 is preferably rotatable about the optical axis 232 of the movable lens 228 to accommodate for differing pupilary distance. Both prisms 226, however, could alternatively translate horizontally (e.g., parallel to the x-axis) along with the movable lens to accommodate the subject's pupilary distance. The movable lens 228 is preferably held by a movable mount that can be translated axially along the optical axis 232.

Preferably, the movable lens 228 comprises a computer-controlled moveable lens. This moveable lens 228 may be motor driven in various embodiments. In operation, the lens 228 is preferably translated to an axial position at a location that is longitudinally displaced with respect to the prism 226 to provide spherical correction. The purpose of the prism 228 is to correct the image left to right and top to bottom, since the moveable lens 228 inverts and flips the image. The movable lens 228 may alternatively comprise a plurality of lens or other optical elements. In certain preferred embodiments, the movable lens 228 comprises two movable and rotating cylinder lenses to provide both spherical and astigmatic correction for the subject. The movable lens 228 may comprise a plurality of refractive optical elements or other optics that includes correction for other aberrations such as other high aberrations. In various embodiments, the movable lens 228 may include an adaptive optical element to provide optical correction as described above. This adaptive optical element may be used in conjunction with or instead of the moveable lens 228. This adaptive optical element may correct for higher order aberrations. For the majority of patients, however, spherical correction is sufficient to allow the patent to fixate on the target.

The adaptive optical element comprises an optical element with beam shaping properties that are re-configurable. The adaptive optical element may, for example, comprise a deformable mirror having a shape that may be selectively altered. In some embodiments, one or more transducers such as piezoelectric transducers may be disposed with respect to different portions of a mirror to apply stress to the mirror to alter the shape of the mirror. Other types of deformable mirrors are possible. Adaptive optic mirrors are available from Boston Micromachines Corporation, 108 Water Street, Watertown, Mass. 02472 as well as Flexible Optical B.V., P.O. Box 581, 2600 AN, Delft, The Netherlands. Other types of adaptive optical elements may be employed as well. The adaptive optical element, may for example, comprise refractive, diffractive, or reflective optical elements or combinations thereof. Various approaches to altering the optical parameters of the optical element are also possible. One or more adaptive optic elements may be employed as well.

In the optical path 216 to the right of the movable lens 228 in FIG. 7 is a movable mirror 234 and an internal fixation target 236. Such a mirror 234 and internal target 236 is preferably included in the visible optical path 216 for each eye 218. The movable mirror 234 is used to divert the subject's field-of-view. For example, these mirrors 234 can be rotated or moved into the field-of-view or optical path 216, allowing the subject to view an image of the internal fixation target 236 within the instrument 210. A lens 238 may be placed between the mirrors 234 and the internal target 236 to position the images of the internal target at the desired image distance. Multiple images can be placed at different distances and used to present the subject with both near and far target images. A single pair of images and movable lenses 228, one for each eye 218 can be used. Alternatively, two different lenses 238 or sets of lenses of differing focal lengths, one for each eye 218, can also be used to generate different perceived distances for the different eyes. The images can also be stereoscopic in nature to provide a three-dimensional effect, adding additional reinforcement to the desired image depth.

Accordingly, depending on the setting, the visible look-through module in FIG. 7 may comprise the optical path 216 from the look-through eye-piece to a target 270 at about a 20 foot distance or to the internal target 236 within the instrument 210. In addition, the visible look-through path 216 includes the lens 228 on the moveable translation stage to correct the patient's vision based on measurements of the wavefront sensor 210, allowing a patient needing large amounts of correction to relax and focus. The movable mirror 234 may be placed after the lens translation stage and can be rotated or moved into and out of the optical path 216. When rotated into the optical path 216, the mirror 234 redirects the patient's vision onto the pair of internal fixation targets 236. Two internal target sets are preferably built into the instrument 200, one presenting an image at a simulated reading distance and the other at a relatively farther distance. With the mirror 234 rotated out of the optical path 216, the patient can look through the system 200 at a real target located at a relatively far distance. The flexibility of the visual optics path 216 allows the patient to look at a target after pre-correction for measured focus. The instrument thus offers flexibility in OD or MD protocol—near vs. far, fogging vs. internal focusing, pre-corrected or uncorrected, and other combinations that can be used during measurement. A patient's accommodation range may also be measured, for example, by repositioning the lens 228 so as to provide different levels of correction. The patient's ability to handle the different levels of correction by accommodating may be measured such as, for example, using technology described in U.S. Pat. No. 6,761,454 entitled "Apparatus and Method for Determining Objective Refraction Using Wavefront Sensing" issued to Lai et al on Jul. 13, 2004, and U.S. patent application Ser. No. 10/653,552 entitled "Apparatus and Method for Determining Subjective Responses Using Objective Characterization of Vision Based on Wavefront Sensing" filed Sep. 2, 2003, which are both incorporated herein by reference in their entirety.

A light source 240 may illuminate the internal fixation target 236. This illumination source 240 may, for example, comprise a light source such as a light emitting diode (LED) or an incandescent light bulb electrically powered and connected to control electronics for controlling the brightness of the source. Illumination intensity for the internal target images can be controlled, e.g. through a computer and calibrated to specific levels. Illumination may, for example, be controlled to simulate particular environments such as indoors, outdoors, offices, night driving, etc. When combined with the analysis of the pupil size determined from the wavefront sensor 210, detailed pupil reaction with respect to illumination level information can be recorded. For example, in various embodiments the sensor can image the pupil and thus pupil size can be correlated with illumination level.

As discussed above, the instrument 300 further comprises the wavefront sensor 210 such as the self-imaging systems described above. Accordingly, in various preferred embodiments, this wavefront sensor 210 preferably employs a two-dimensional periodic pattern 242 and a camera 244 at or focused on a self-image plane or Talbot plane of the periodic pattern. In certain preferred embodiments, this periodic pattern 242 comprises a checkered pattern as discussed above. This wavefront sensor 210 is disposed to receive light transmitted through the IR/Visible beamsplitter 220 and is preferably mounted onto either a manual or computer-controlled XYZ stage 246 to accommodate such positioning. As illustrated in FIG. 7, this wavefront sensor 210 may comprise an optical relay 248 comprising two lenses 250, 252. A fold mirror 254 may be disposed between these two lenses 250, 252 or elsewhere preferably to make the overall design more compact. The relay lens system 248 may be aligned along an optical path 256 that includes the periodic pattern 242 and the camera 244.

An adaptive optical element (not shown) may also be inserted in a portion of the path 256 through which light also passes to the wavefront sensor 210 such that the adaptive optical element operates as null optics for the wavefront sensor as described above. Software could "null" or cancel the wavefront for the sensor 210, which would result in the subject's vision being optimally corrected as well.

Control signals from a controller or control module (not shown) such as a microprocessor or control electronics may be used to control the operation of the adaptive optical elements. A feedback loop may be included from the detector 244 or associated computing components to the controller. Feedback may be provided from measurements obtained by the detector 244 or computing components that calculate values based on the shape of the wavefront projected through the eye 218. This feedback may be used to determine suitable adjustment to the wave-shaping properties of the adaptive optical element.

The adaptive optical element may correspond to null optics that provide correction to offset the aberrations in the eye 218.

Correction of high-order aberrations and correction of lower order aberration terms such as focus and astigmatism may be provided by the adaptive optical element to neutralize substantially all the aberrations from the eye 218. In other embodiments, the adaptive optical element may be employed in conjunction with null optics, which correct for lower order aberrations like spherical aberration and astigmatism. Using the adaptive optics mirror in conjunction with one or more null lens that correct, e.g., for spherical aberration and astigmatism, would allow the use of less expensive adaptive optics elements such as shorter stroke adaptive optics mirrors.

In various preferred embodiments, the moveable wavefront sensor stage 246 shown in FIG. 7 may be disposed so as to move the wavefront sensor 210 between the two different eyes. In one position, for example, the stage 246 may be positioned such that the wavefront sensor 210 images the left eye while the stage may be translated to another location such that the wavefront sensor images the right eye. This stage 246 may allow the wavefront sensor 210 to be moved in the optical path of the respective eyes, lining the eye 218 up in the center of the sensor 244. If a computer controlling the stage 246 is employed, a software routine can be introduced to analyze the position of the eye 218 with respect to the wavefront sensor 210 and provide the necessary stage movement to line up the wavefront sensor with the optical centers of the two eyes. Although not shown in the schematic drawing of FIG. 7, separate oculars or eyepieces 312 may be used for each eye 218. The visible and IR optical paths 216 and 256 preferably pass through these oculars 312. The wavefront sensor stage 246 may be translated to suitably align the wavefront sensor 210 with the optical path through the respective ocular 312. A computer or image processing electronics may determine the edge and center of the pupil of the respective eye. In various embodiments, the size center of the pupil is determined from the wavefront sensor 210. Additionally, the distance between the two eyes (pupilary distance) can be determined from the movement of the wavefront sensor 210 and the location of the pupil within the images.

The wavefront sensor 210 may further comprise illumination optics 266 that includes a light source 258 for illuminating the eye 218. This light source 258 may comprise, for example, a laser diode such as an infrared laser diode. Other types of lasers may be employed in this system 200 as well. In various embodiments, the laser produces a narrow substantially collimated beam 270. In some cases, therefore, collimating optics such as a collimating lens is not needed. The light source may alternatively comprise a super luminescent diode. Other types of light sources including other types of light emitting diodes may also be employed. Focusing or collimating optics 260 and a pin hole 262 may be included with the super luminescent diode or light emitting diode and disposed along an optical path 268 as shown FIG. 7. In other embodiments, a light emitter such as a laser diode or super luminescent diode may be focused onto a fiberoptic which outputs light that is collimated into a small beam by a lens. Other configurations and methods for providing illumination are possible and are considered to fall within the scope of the invention.

Preferably, the light beam 270 directed into the eye 218 is substantially narrow. In various preferred embodiments, the divergence of the beam 270 propagating to the eye 218 is sufficiently small and the beam is sufficiently narrow such that a cross-section across the beam orthogonal to its propagation direction is less than the size of the pupil. Preferably, the beam 270 has a cross-sectional dimension such as diameter or width that is substantially less than the average diameter of the pupil. The pupil may, for example, be on average between about 4 to 8 millimeters, e.g., 6 millimeters. In various preferred embodiments, the diameter or width of the beam 270 directed through the pupil is less than about 1 millimeter across and may be between about 200 to 600 micrometers (µm), e.g., about 400 µm in diameter. The beam 270 is preferably small so as to reduce the affect of aberration of the eye 218 on the beam. Preferably, the beam 270 is sufficiently small that the aberration in the eye 218 does not alter the beam entering the eye and does not increase the size or deform the shape of the light spot formed where the beam is incident on the retina. Preferably, this light spot formed on the retina is substantially small, for example, with respect to the ocular lens and cornea and approximates a point source. Blurring, increasing the size of the light spot, and/or distorting the shape of this spot may have a negative affect on the wavefront measurements.

A beamsplitter 264 may be inserted in an optical path 256 to the periodic pattern 242 and camera 244 so as to direct the beam 270 to the eye 218. Alternative configuration may also be employed.

To measure the refractive properties of the eye, the optical instrument 200 uses the several optical modules described above with respect to FIG. 7: the visual optics or visible look-through module 212, the illumination optics 266, and the wavefront sensor 210. The illumination optics 266 illuminate the eye 218 preferably with invisible (e.g., IR) radiation. This invisible radiation propagates along the optical path 268 from the light source 258, to the eye 218, reflecting off the beamsplitter 264 between the light source and the eye. Accordingly, a near-infrared light beam 270 may be injected into the eye. Light from this light beam 270 is then scattered off the retina back through at least a portion of the injection path. The wavefront sensor 210 senses this invisible radiation reflected from the eye 218. The near-infrared light propagates through the IR/visible beamsplitter 220 as well as the 90%/10% injection beamsplitter 264 along the wavefront sensor path 256.

This wavefront sensor 210 preferably provides very high-resolution wavefront information, as discussed above. This instrument 300 preferably offers enough resolution to measure relatively sharp phase errors near the edge of the pupil, for instance, and can handle high-frequency wavefront errors that might occur as a result of prior surgical procedures. After the wavefront data is taken and analyzed, the wavefront analysis results are then displayed on the screen near the device and can be encoded into barcode format or transferred electronically. The Zernike data may for example be encoded in a barcode along with the other information such as, e.g., patient ID, left/right eye, and may be sent to a lab for processing of the lens. In various embodiments, the instrument may be linked to an office practice management system via wireless network, intranet, or internet. Ethernet may be used. As described above, the office practice management system may include one or more computers or microprocessors and may also include storage or memory for recording measurement and patient data. The office practice management system may be in linked with insurance providers, other healthcare providers, lens and eyewear facilities manufacture or sales facilities, etc., and accordingly information may be conveniently communicated to such destinations.

Figure 8:
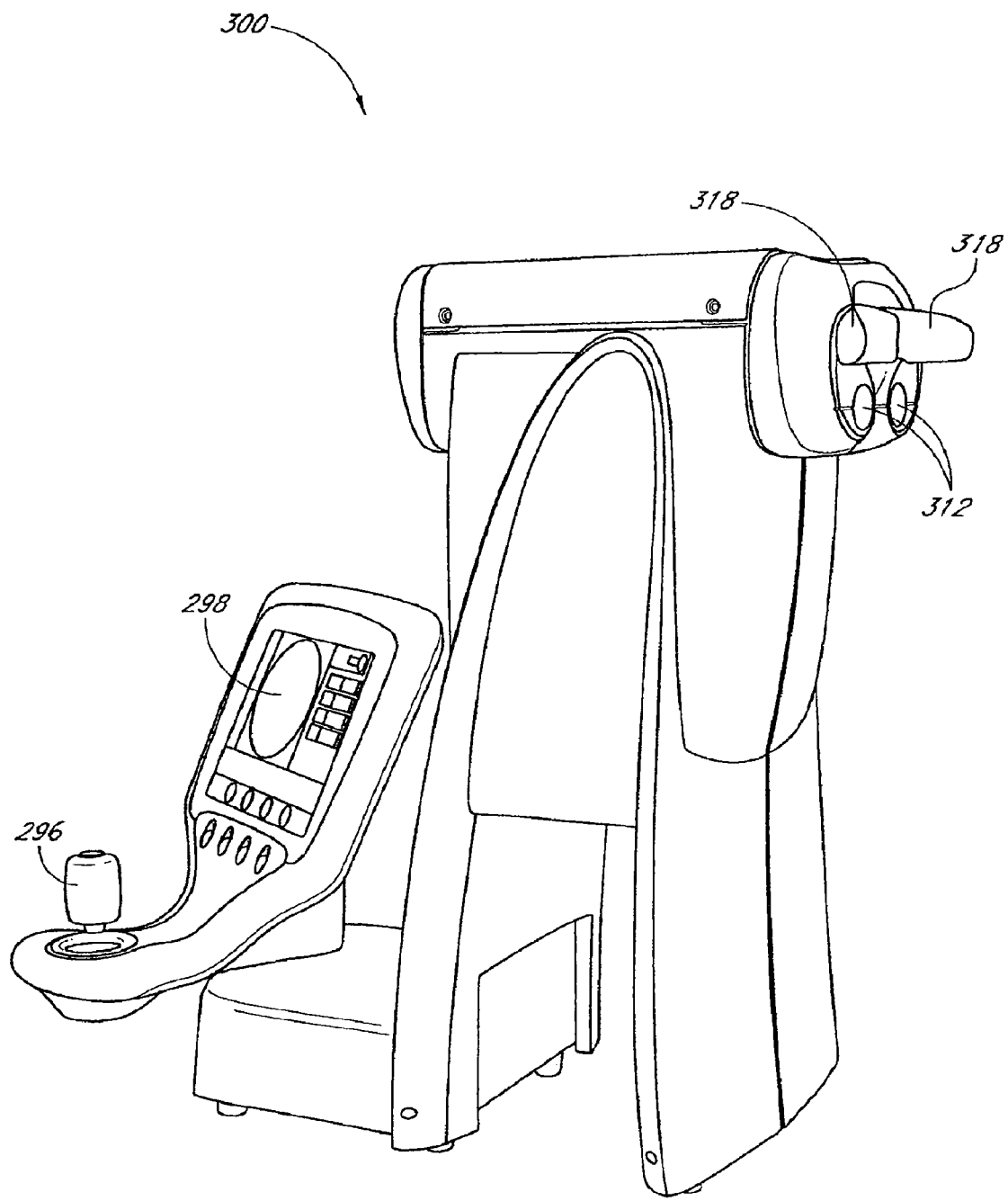
FIG. 8 is a full perspective view of the exterior of the instrument that can be configured to measure spectacle lenses as well as the refractive properties of a person's eyes.

Embodiments of the instrument 300 may include a small computer and/or electronics circuitry that handle the motion control of the motors or other translation devices, on/off and intensity control of the multiple illumination sources 240, 258, as well as reading sensors located throughout the system 300. In an embodiment shown in FIG. 8, positioning of the wavefront sensor 210 is accomplished via a fly-by-wire joystick control system 296 similar to a video game. The joystick 296 operates three motors giving the three degrees of freedom required for positioning. Computerized, microprocessor or electronically controlled automation of sensor positioning is possible. As shown in FIG. 8, the system 300 is preferably designed with the ergonomics of the patient and operator in mind, and may be packaged with a striking look and feel. The instrument 300 also preferably includes a display screen 298 for example for displaying the pupil and/or results of wavefront measurements.

Preferably, the ocular measurements may be performed without causing discomfort to the patient. Advantageously, since the measurement is fast, there is no need for rigid restraint on the patient during the exam. The comfort level of the patient is enhanced through the use of the invisible near-infrared laser 58, e.g., at a wavelength of about 850 nm, which forms a spot on the retina and illuminates the optical path 256 from the ocular surface to the detector in the wavefront sensor camera 244. Due to the efficiency of the optical measurement, a much lower power beam can be used to illuminate the retina. The power, for example, may be lower by a factor of approximately 4-7 compared to other conventional instruments that perform wavefront measurements on the eye. The combination of the use of infrared light and the lower illumination power level may lead to increased comfort and safety.

During an exam, a sequence of short exposures is preferably taken at one setting, which involves only one initial alignment of the patient. The patient is in the chair for only a few minutes, and the results are ready to display to the operator in less than one minute. Additional details regarding systems for measuring refractive properties of the eye is disclosed in U.S. patent application Ser. No. 10/971,769 entitled "Ophthalmic Diagnostic Instrument" filed by Warden et al on even date herewith, which is incorporated herein by reference in its entirety.

Figure 9A:
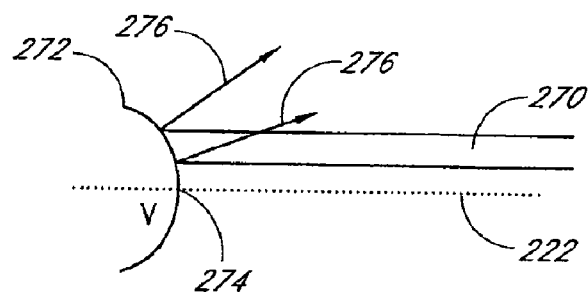
FIGS. 9A-9D are schematic drawings illustrating different embodiments of the invention for illuminating the eye.

Various techniques may be employed to improve the operation of the instrument 300. For example, in various preferred embodiments, this beam of light 270 is parallel to but laterally offset from the optical axis 222 of the wavefront sensor 210 as shown in FIG. 9A. Accordingly, the beam of light 270 is incident on the cornea 272 at a location offset from the vertex 274 of the cornea. Displacing the beam 270 away from the vertex 274 or center of the cornea 272 reduces retro-reflection of a portion of the light beam back along the optical axis 222 and into the wavefront sensor. Such retro-reflection may cause error in wavefront measurements. As illustrated in FIG. 9A, offsetting the beam 270 incident on the eye 218 laterally with respect to the vertex 274 of the eye 218 causes light reflected from the cornea 272 (represented by rays 276) to be directed at angles with respect to optical axis 222. This retro-reflected light 276, therefore, does not propagate back down the optical axis 222 and into the wavefront disrupting wavefront measurement.

Figure 9B:
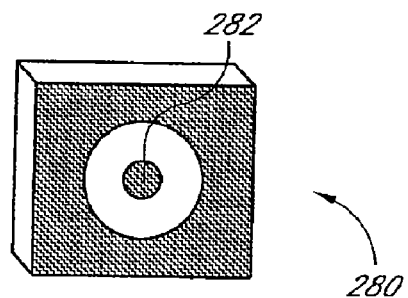
Figure 9C:
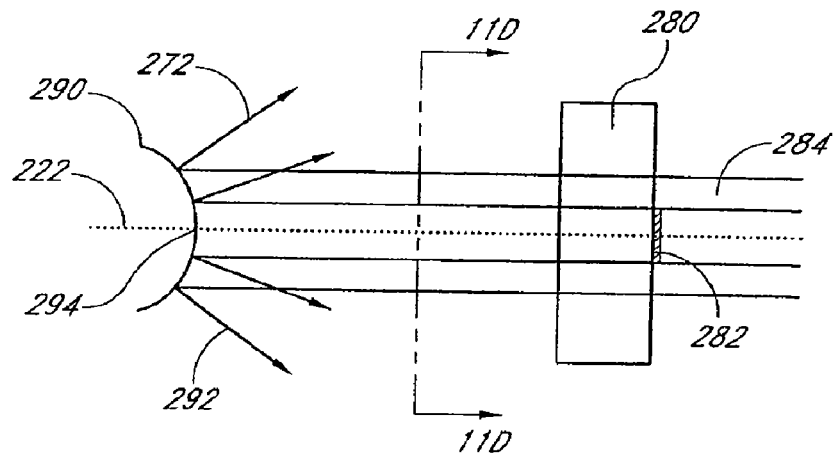
Figure 9D:
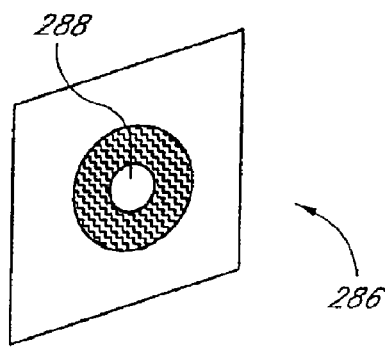

Other ways of more efficiently coupling light into the eye 218 are possible. For example, in some embodiments, the beam 270 from the light source 258 is introduced directly down the optical axis 222 of the sensor 210. In such cases, an optical element 280 (see e.g., FIGS. 9B-9C) having a central obstruction 282 may be inserted in the path of the beam 284 so as to produce an annular or doughnut shaped beam cross-section 286 (shown in FIG. 9D) having a central obscuration 288 or dark region. Such a configuration would increase the amount of light that could be injected into the eye 218, however, light retro-reflected by the cornea 290 (represented by rays 292) along the optical axis 222 directly into the wavefront sensor could be reduced. The annular shaped beam would intersect regions of the cornea 290 off-center from the point 294 where the optical axis 222 intersects the cornea (i.e., the vertex). Reflections from the cornea, therefore, would not be reflected back along the optical axis 222 into the wavefront sensor. The obstruction 282 and corresponding obscuration 288 need not be centrally located and need not form a perfectly annular beam profile although a central obscuration may be preferred in some embodiments. In certain preferred embodiments, a lens (not shown) may be included in the optical path after the central obscuration 288 to image the obscuration pattern onto the eye 218. Such a lens may also compensate for the spherical error in the subject's eye 218 who may be near-sighted or far-signed. In such case, the lens may be used to offset the affect of the spherical error in the subject's eye 218 and thereby aid in focusing the beam 284 into a narrow spot on the retina of eye. The pattern of the obscuration 288 reaching the eye 218 may be either diverging or converging depending type of lens used, which depends on the sign of the subject's spherical error.

As discussed above, in addition to measuring the refractive properties of the eye, the instrument 300 can be employed as a lensometer. In various embodiments, the instrument 300 is configured to position a spectacle lens or contact lens such that the waveshaping properties of such corrective lenses may be measured.

Figure 10:
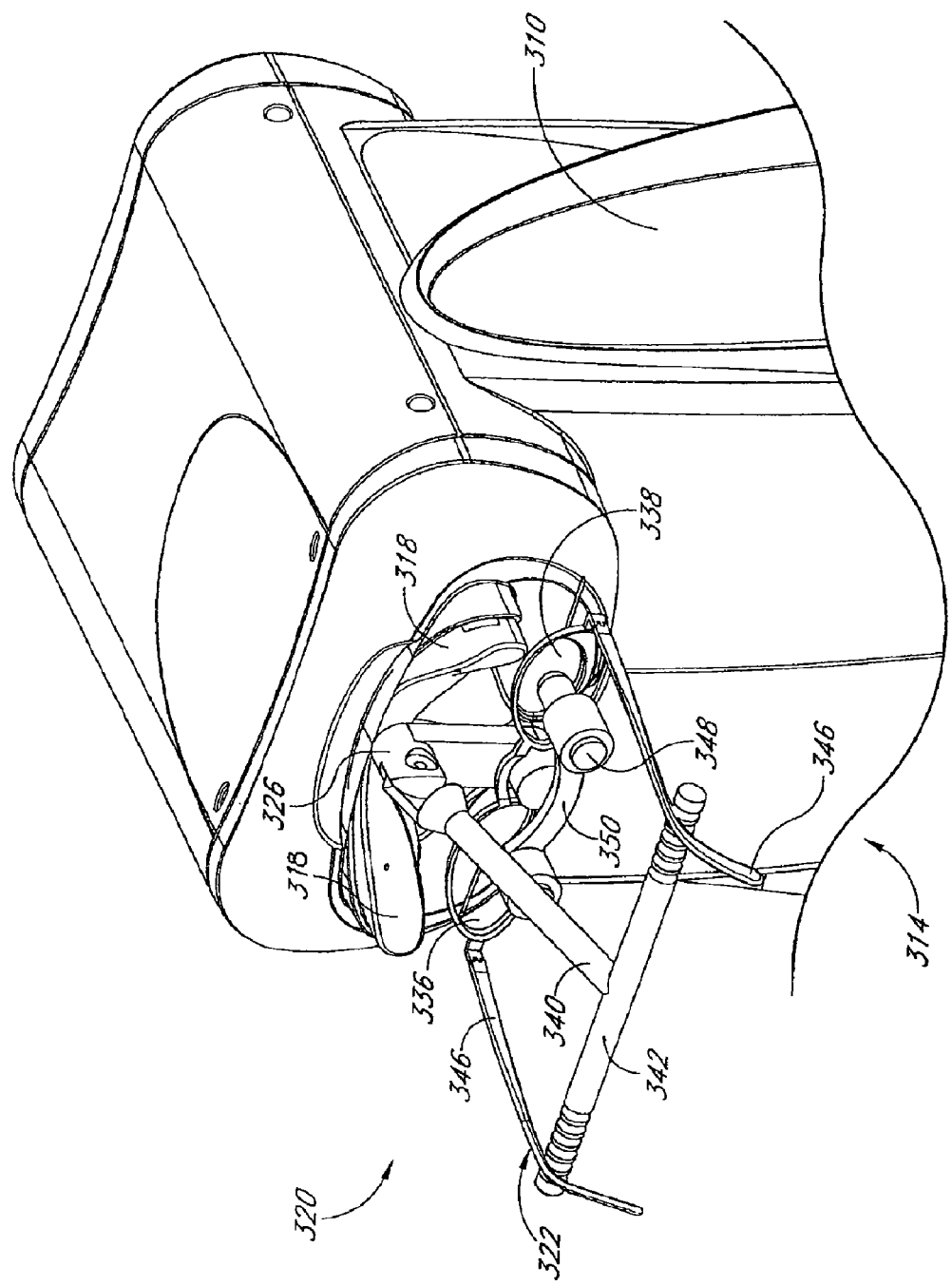
FIGS. 10 and 11 are perspective views of an adapter for configuring the instrument to measure eyeglass lenses.
Figure 11:
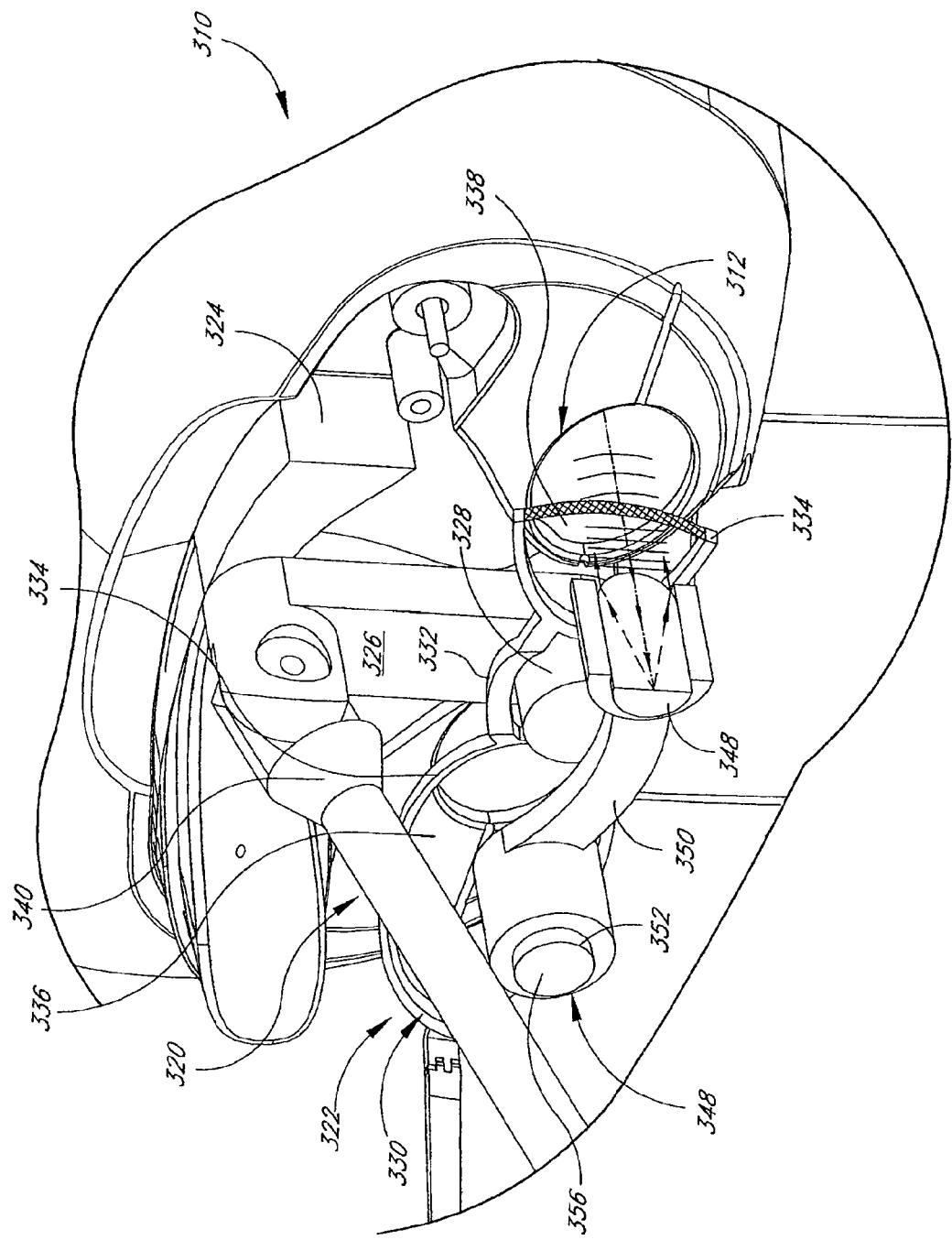

In embodiments such as those shown in FIGS. 10 and 11, for example, the instrument 300 is outfitted with an adapter 320 for supporting a pair of spectacles 322. In certain embodiments, the adapter 320 can be added proximal to the forehead rests 318. The adapter 320 is mounted to a crossbar 324 (see cutaway in FIG. 11) and includes a central upright support 326. The crossbar 324 can be secured to the front face 314 of the instrument housing 310 above the oculars 312. As shown, in various preferred embodiments, the central upright support 326 is connected to the crossbar 324. Although referred to as a crossbar 324, the structure should not be limited to a bar but may comprise other types of fixtures such as but not limited to elongate members, plates, and other structures for mounting the adapter 320 to the instrument housing 310. Also, although the adapter 320 is connected to the instrument housing 310, in other embodiments the adapter may be attached to the frame or otherwise secured in place. Other configurations are also possible. The adapter 320 may be secured to the instrument 200 with screws or bolts or other types of fasteners. Preferably the fasteners can be readily attached to or removed from the instrument housing 310 to permit quick and easy connection and detachment of the adapter 320. Clips, clamps, clasps, pins, plugs, magnets, slides, are examples of fasteners that may be employed. Other types of fasteners, however, may be used as well. In some embodiments, the adapter 320 may comprise through holes. A connector may be attached to the front face 314 of the instrument housing 310 for mounting the adapter 320 thereto.

As shown in FIGS. 10 and 11, the central upright support 326 comprises a spectacle holder 328 for supporting and holding the spectacles 322 in place. The spectacles 322 may comprise a frame 330 having a nosepiece 332 connected on opposite sides to left and right rims 334 in which left and right lenses 336, 338 are mounted. The nosepiece 332 may rest in or on the spectacle holder 328 attached to the upright support 326. A fastener or other locking mechanisms may be provided to secure the frames 330 to the spectacle holder 328. Accordingly, the frames 330 can be safely secured to the adapter 320 and positioned with respect to the lensometer for measurement.

The central upright support 326 is also connected to an earstem holder arm 340 having a crossbar 342 for supporting a pair of earstems 346 on the spectacles 322 (see FIG. 10). The earstem holder arm 340 shown in FIGS. 10 and 11 is connected to the central upright support 326 through a hinge. This hinge preferably permits the earstem holder arm to fold down in position to orient the spectacles lens 336, 338 in front of the oculars 312. Other designs are possible and the spectacles 322 may be properly oriented and position using other techniques.

The adapter 320 further comprises a pair of retro-reflectors 348 disposed with respect to the left and right spectacle lenses 336, 338 such that the left and right spectacle lenses are between the retro-reflectors and the respective oculars 312. As a result, an optical path extends from the ocular 312, through the lens 336, 338 and to the retro-reflector 348 for each of the right and left spectacle lenses. The retro-reflectors 348 are supported by a holder 350 attached to the central upright support 326. The retro-reflector holder 350 may comprise a pair of arms extending from the central upright support 326 that position the retro-reflector 348 proximal to the spectacle lenses 336, 338.

Figure 12:
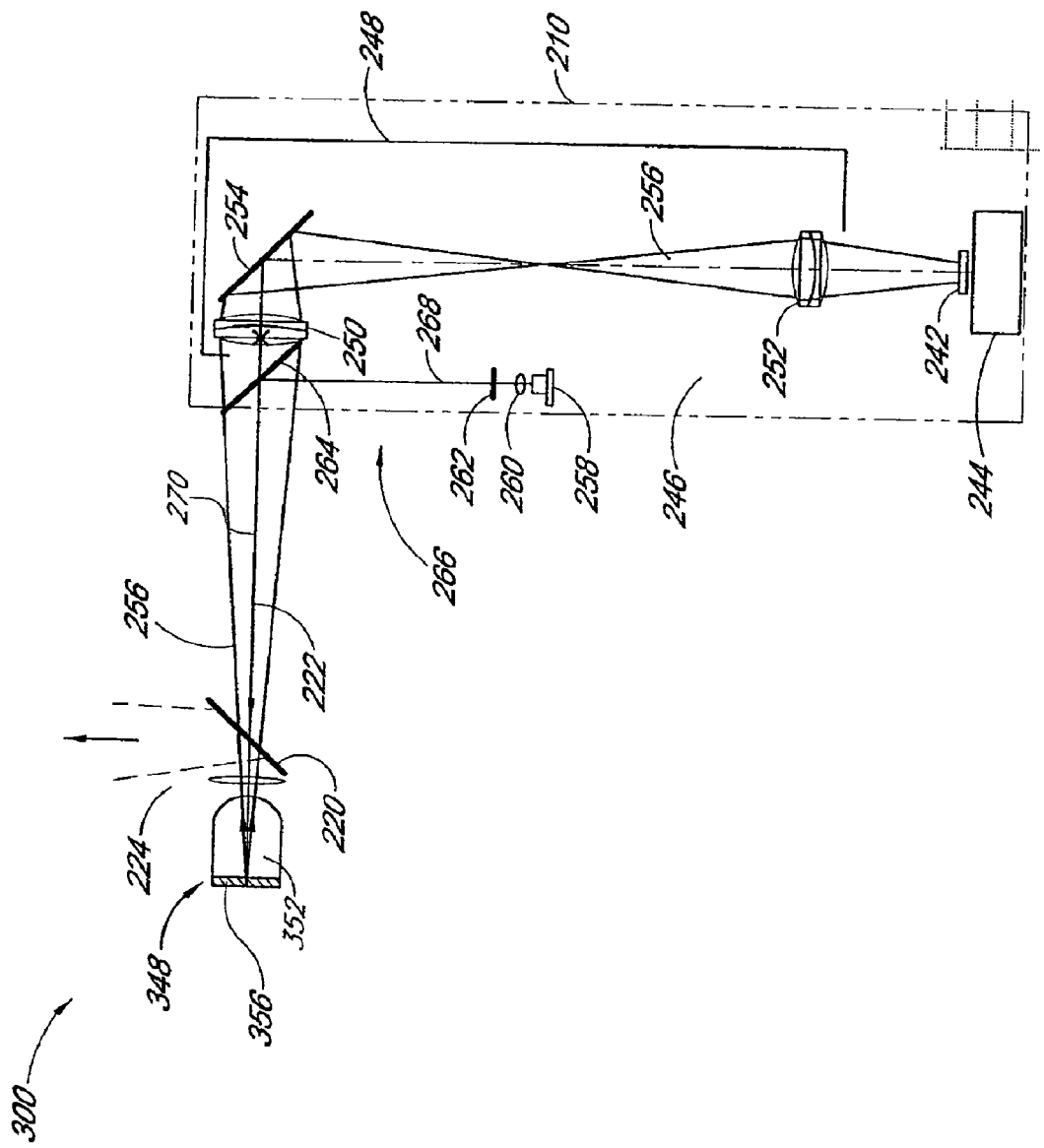
FIG. 12 is a schematic diagram of the optical instrument configured as a lensometer.

A cross-section of one of the retro-reflectors 348 is shown in FIG. 12, which is a schematic diagram of the optical instrument 300 configured as a lensometer. The retro-reflectors 348 may comprise a substantially optically transmissive rod 352 having a curved front face 354 and reflective rear face 356. This rod 352 may, for example, comprise glass or plastic in certain embodiments. The reflective rear face 356 preferably is diffusely reflective. In various preferred embodiments, the reflective rear face 356 has reflective characteristics similar to that of the retina. In some embodiments, the reflective rear face 356 comprises a substantially planar face formed on the glass or plastic rod 352 coated or painted with reflective material. The rear reflective face 356, for example, may be painted with black paint that is diffusely reflective and that may have a reflectivity of between about 2 to 10% at the specified wavelength of the excitation beam 270 in some embodiments. The rear reflective surface 356 may be textured or have microstructure that diffusely reflects light. Other designs are possible.

The diffusely reflected light is collected by the curved front face 354 such that the beam 270 is expanded. The front face 354 may also have a shape and curvature and be positioned with respect to the rear face 356 such that light scattered from the diffusely reflective rear face 356 is collimated. In some embodiments, this curvature may be substantially spherical. In addition, the radius of curvature of the front face 354 may be preferably about the distance from the front face to the rear face 356 as measured along the central optical axis through the rod 352. The front face 354 preferably operates as a lens forming a beam from light reflected from the rear face 356. In various preferred embodiments the front surface 354 collimates the light reflected from the diffusely reflective rear surface 356. The front surface 354 may be shaped differently in different embodiments and may comprise other types of surfaces and optical elements. For example, the front surface 354 need not be a conventional refractive lens surface. The front surface 354 may comprise a diffractive surface having diffractive features formed thereon, thereby forming a diffractive or holographic optical element. The front surface 354 may also contribute to the beam shaping, however, work in conjunction with one or more other optical elements and/or surfaces. The front surface may also be planar in some embodiments. An additional lens element may provide beam shaping. Alternatively, gradient refractive indices of the rod 352 or other optical element may provide beam shaping. Other configurations are possible.

Preferably, however, a beam of light is propagated through the ocular 312. This beam of light 270 may originate from a light source similar to the light source 258 shown in FIG. 12 and may follow an optical path similar to the optical path 266 shown in FIG. 12. As discussed above, the light beam 270 may be offset from the vertex of the spectacle lens and the center of the front face 354 of the rod 352 so as to reduce back reflection. Alternative illumination schemes are possible. For example, the beam 270 may have an annular cross-section as discussed above to reduce light reflected from spectacle lens and the front face 354 of the reflector 350 back into the wavefront sensor. To produce such a beam having an annular cross-section, an optical element having a central obstruction may be employed. The light may, for example, be passed through an aperture having a central obstruction to introduce the obscuration into the beam. Although an annular beam formed by a central obscuration may be used, in some embodiments, the beam has a dark region that is not centrally located.

In other embodiments, the reflective element 348 is replaced with an external light source, such as a diode laser, and possibly a beam expander and/or collimator optics. Measurement of the corrective lens such as spectacle lens are performed using the beam provided by this additional light source. During measurement of a spectacle lens, the laser located within the wavefront sensor is turned off, blocked, diverted, etc.

In some embodiments, a corrective lens may be measured together with the eye by directing the beam through the corrective lens into the eye and measuring the return from the eye that again passes through the corrective lens. Such a configuration enables the practitioner to characterize the vision as corrected. Spectacles and especially contacts may be measured in this manner. The spectacles and contact lenses may be removed to measure the eyes without correction.

Disadvantageously, light from the beam passed through the lens or introduced into the eye may reflect or scatter back into the camera and can cause an unwanted glint artifact. This undesirable glint presents difficulty in the performing wavefront measurements. Special processing, however, may be employed to reduce the extent that glint, reflection, or back scattering from the spectacles, the eye, or from elsewhere in the optical path corrupts the measurements.

Figure 13:
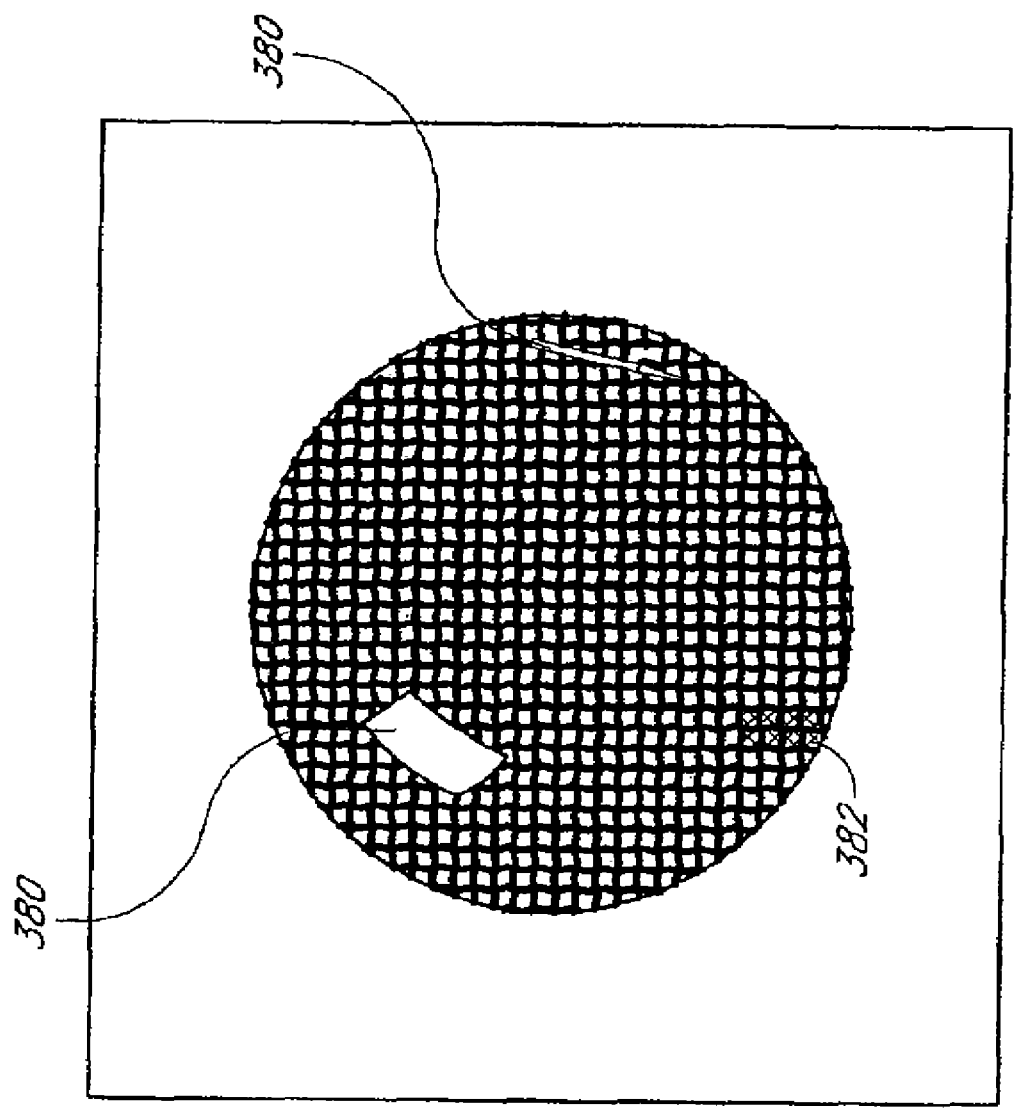
FIG. 13 is an exemplary image of a lens and modulation pattern obtained by the camera focused on the Talbot plane that shows glint on the lens as well as scatter from scratches in the lens and a low contrast region.

Reduced contrast may also result from light specularly or diffusely reflected or backscattered from surfaces of the spectacle lens, contact lens or lens blank as well as from scratches on the optical surfaces, or dust, particulates, or other scatter features in or on the lens or lens blank. Alternatively, light may also be reflected from or scattered by surfaces or features in or on the eye causing reduced contrast. For example, light may be specularly or diffusely reflected from surfaces on the cornea or ocular lens. Light may also be reflected or scattered by features in or on the cornea or the ocular lens as well as in the vitreous and aqueous humor or elsewhere in the eye. Such reflection and scattering may produce bright regions 380, such as shown in FIG. 13. These bright regions 380 may complicate processing. Reduced contrast of the self-image of the grating may also occur at certain locations 382. These reduced contrast regions may also result from reflections and scattering, for example, from scratches or other scatter features or may be otherwise created. The variations in brightness and/or contrast may introduce irregularities or cause saturation or produce relatively high levels of noise in comparison with signal and disrupt the measurements. In many cases, however, processing may be employed to reduce such deleterious effects on the measurements.

Figure 14:
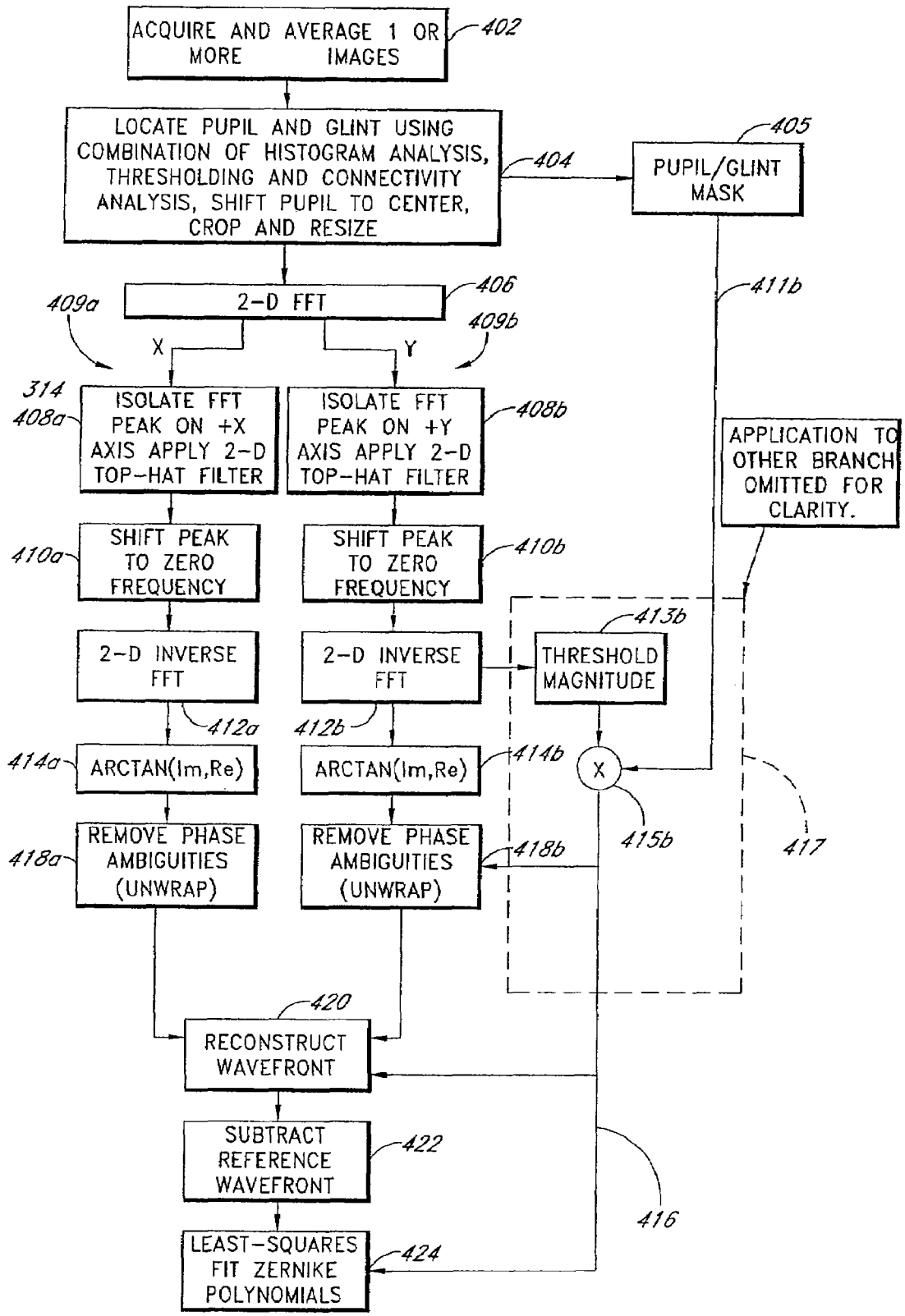
FIG. 14 is block diagram illustrating the processing of data from the wavefront sensor.

A block diagram that describes the processing employed to characterize the wavefronts and determine the wave-shaping properties of the corrective lens or eye or other substantially transmissive optical structure is shown in FIG. 14. This block diagram also shows additional processing used to address artifacts caused by glint and low contrast regions.

Logic may be executed in accordance with processes and methods described with reference to FIG. 14 and elsewhere herein. These and other representations of the methods and processes described herein illustrate the structure of the logic of various embodiments of the invention which may be embodied in computer program software. Those skilled in the art will appreciate that the flow charts and description included herein illustrate the structures of logic elements, such as computer program code elements or electronic logic circuits. Various embodiments include a machine component that renders the logic elements in a form, for example, that instructs a digital processing apparatus (that is, a computer, controller, processor, etc. or portions thereof) to perform a sequence of function steps corresponding to those shown. The logic may be embodied by a computer program that is executed by the processor 34 as a series of computer- or control element-executable instructions. These instructions may reside, for example, in RAM or on a hard drive or optical drive, or the instructions may be stored on magnetic tape, electronic read-only memory, or other appropriate data storage device that can be dynamically changed or updated. Other configurations are possible.

Accordingly, the logic of the processor 34 can be appreciated in reference to FIG. 14. As discussed above, the wavefront of the beam passes through the periodic diffractive element where diffraction effects cause a self-image of the element 28 to appear at the self-image planes. As illustrated in a first block 402, an image of one of the self-image planes is recorded, for example, with a CCD or CMOS detector-based camera. One or more images may be recorded and averaged. The image or images may be transformed into an array of data produced by the detector array and possibly accompanying electronics. The recorded image data may correspond to an array of values correlated to the brightness or amount of light received in a plurality of localized regions of the detector such as single detector pixels. In some embodiments, for example, the detector comprises a 1280×1024 pixel detector array. The detector array may map to a similarly sized data set (e.g., a 1280×1024 data array). Accordingly, the array of data may also be referred to herein as comprising a plurality of pixels. Other size detector arrays and data sets may be employed. Additional processing may be implemented on data received by the detector array and data gathering, storage, and processing arrangements and configurations other than those disclosed herein are also possible.

The principle of Talbot plane self-imaging is presented in references such as, e.g., Joseph W. Goodman, *Introduction to Fourier Optics*, The McGraw-Hill Companies, Inc., which include a treatment of interference and wave optics and which is hereby incorporated herein by reference. The formation of the self-image of the periodic element 28 involves the wave nature of light and the periodicity of the element. In a non-limiting, exemplary embodiment, the wavefront incident on the imaging detector 32 can be represented by the following diffraction equation:

$$I(\vec{r}, z) = I_o \cos\left(\frac{\pi \lambda z}{p^2}\right) \cos\left(\frac{2\pi}{p}\left(r_x - z\frac{\partial W}{\partial x} + r_y - z\frac{\partial W}{\partial y}\right)\right) \quad (3)$$

where: $\lambda$ is the wavelength of the coherent wavefront, z is the propagation distance with the associated vector $\vec{z}$ in propagation direction, p is the period of the periodic diffractive element (e.g., distance from the beginning of one element line to the next element line), r is the spatial dimension in the plane of the detector with its associated vector $\vec{r}$, $r_x$ and $r_y$ are the components of the corresponding unit vector, and $$\frac{\partial}{\partial x}$$

and $$\frac{\partial}{\partial y}$$

are directional-derivatives (or, the gradient) of the wavefront "W" that is being measured, in the x and y directions. The dependency of the self-imaging distance on the spectral wavelength of the wavefront and the spatial frequency of the periodic diffractive element is given by:

$$d = \left(\frac{np^2}{\lambda}\right) \quad (4)$$

where n is the integer multiple at which distances the self-images occurs. For example, for a periodic diffractive element having a period, p, of 50 micrometers (μm), this distance, d, may be between about 2.9 to 3.0 millimeters (mm) or in proximity thereto for light having a wavelength of 850 nanometers (nm). Integer multiples of this distance may be appropriate as well.

In the case where the two-dimensional modulation pattern is a two-dimensional sinusoidal function, the intensity pattern at the first Talbot plane (e.g., where $z_T$=2 $p^2/\lambda$) may be represented as follows:

$$I(x, y) = \frac{1}{4}\left(1 + \frac{1}{2}\cos\left(\frac{2\pi}{p}x - p\frac{\partial \varphi}{\partial x}\right) + \frac{1}{2}\cos\left(\frac{2\pi}{p}y - p\frac{\partial \varphi}{\partial y}\right)\right)^2 \quad (5)$$

where I(x,y) is intensity at given x, y, coordinates, $\phi$ is the phase of the wavefront, and p is the period of the 2-D sinusoidal modulation pattern.

In the case where an eye is the object under test, the pupil in the eye may be discernable in the recorded image. Similarly, the aperture of a lens such as a contact lens or a spectacle lens may also be apparent. For example, the image may comprise a dark region corresponding to the iris and possibly other portions of the eye that block light scattered from the retina. The image may further comprise a region corresponding to the pupil area where the light may exit the eye and pass through the two-dimensional modulation pattern onto to the detector. Similarly, when measuring a spectacle or contact lens, the dark region may correspond to regions outside the perimeter of the lens. Light transmitted through the lens will continue through the 2-D modulation pattern illuminating the pattern which may be discerned at the self-image plane. (The resultant image detected by the camera focused on the self-image plane may be similar to FIG. 13, except that the pupil or aperture, etc. need not be in the center.) In some exemplary embodiments, the field-of-view of the camera may be about 12×15 millimeters at the self-image plane with the pupil about 6 millimeters in diameter. The field-of-view for embodiments of the combination aberrometer and lensometer may be similar. For a stand-alone lensometers system dedicated to measuring lenses such as corrective lenses, the field-of-view may be larger, e.g., 20 to 80 millimeters across.

In certain preferred embodiments, the location of the pupil or aperture is determined and a mask may be created with regions outside the pupil or aperture being pulled out (see second block 404). This mask, may comprise a digital filter comprising, for example, an array of values, e.g., 0's and 1's with 0's outside the perimeter of the pupil or aperture and 1's inside the pupil or aperture. At a later stage, this mask may be multiplied with the image data array in some embodiments to eliminate contribution from regions outside the pupil. Additional processing may be employed. For example, in some embodiments, the pupil or aperture is centered and possibly resized for display purposes.

As discussed above and illustrated in a third block 406, a Fast Fourier Transform or other transform may be applied to obtain a spatial frequency representation of the image. This step is also schematically illustrated in FIG. 15A. An exemplary representation of a Fourier transform of a wavefront propagated through a two-dimensional sinusoidal modulation pattern oriented at 45° is set forth in the expression below:

$$F\{I(x, y)\} = \quad (6)$$
$$\delta(f_x - 1/p, f_y) \otimes F\{e^{-jp\frac{\partial \varphi}{\partial x}}\} + \delta(f_x, f_y - 1/p) \otimes F\{e^{-jp\frac{\partial \varphi}{\partial y}}\} +$$
$$\delta(f_x + 1/p, f_y) \otimes F\{e^{jp\frac{\partial \varphi}{\partial x}}\} + \delta(f_x, f_y + 1/p) \otimes F\{e^{jp\frac{\partial \varphi}{\partial y}}\} +$$
$$\text{DC and several other components centered}$$
$$\text{at harmonics of fundamental frequency } 1/p.$$

Figure 15A:
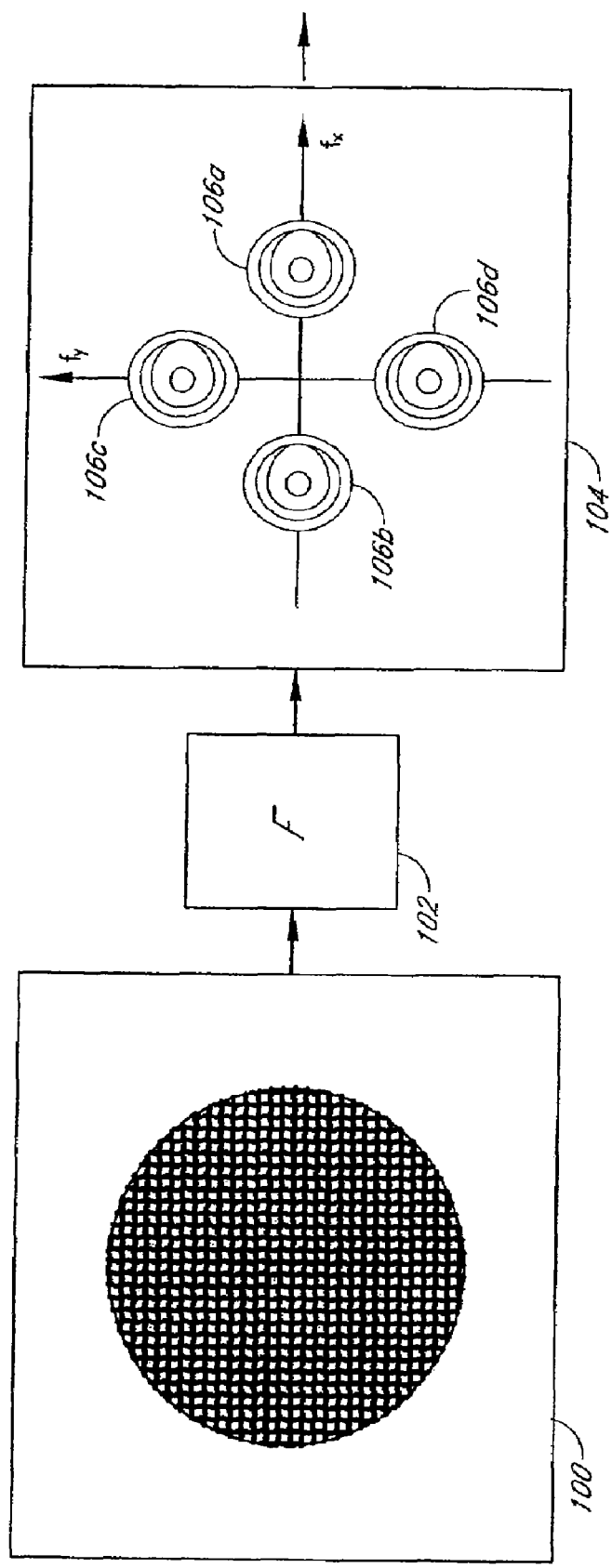
FIGS. 15A-15C are schematic diagrams illustrating one method for converting the image produced at the self-image plane into gradient information corresponding to the wavefront at that self-image plane.
Figure 15B:
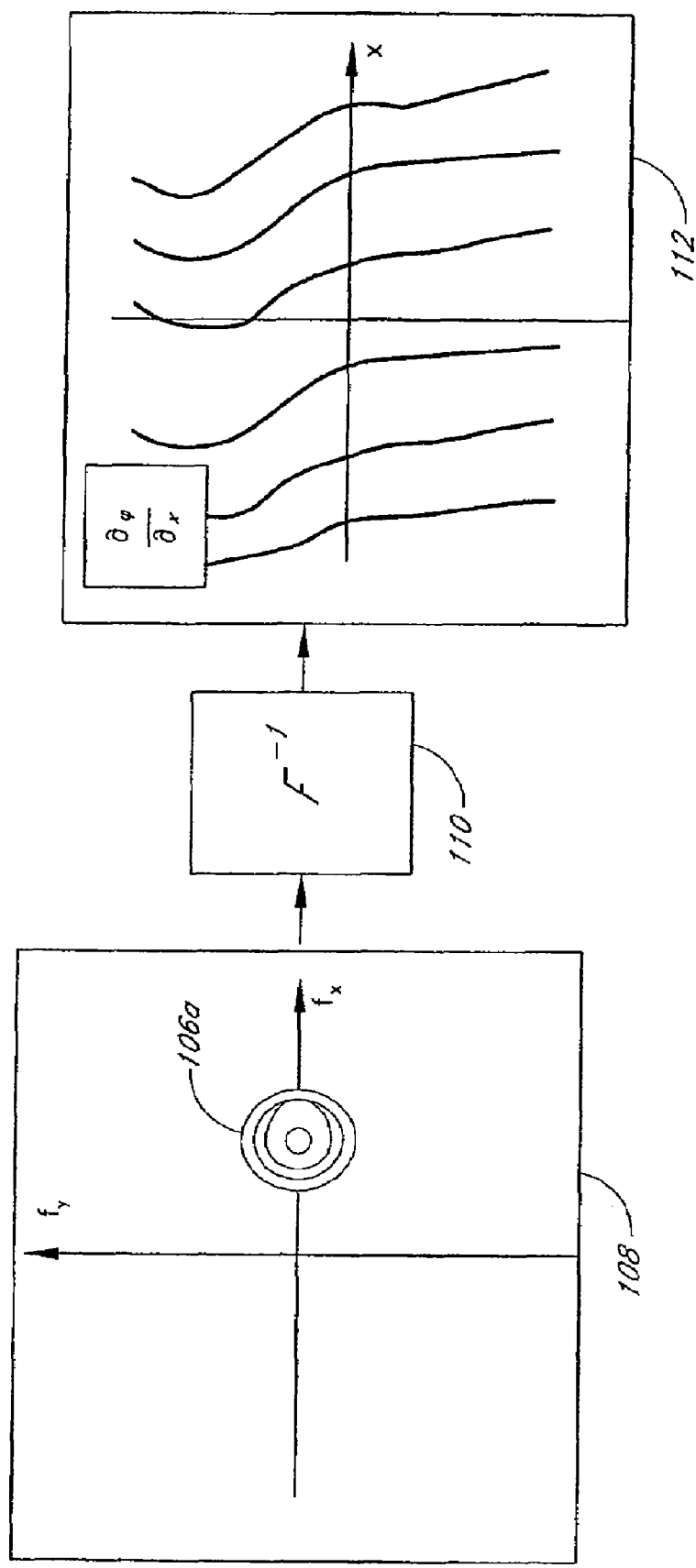
Figure 15C:
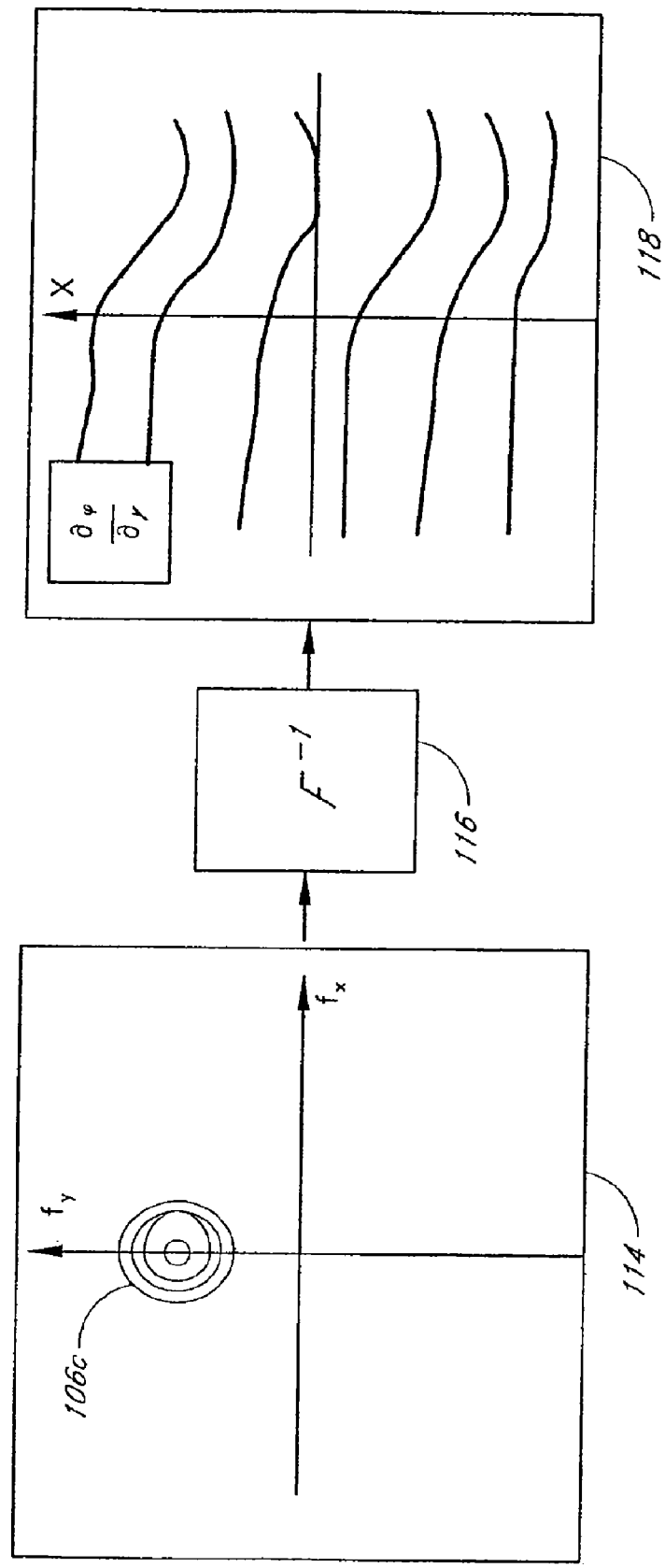

In this equation $\delta(\ )$ corresponds to the impulse function, and $f_x$, $f_y$, are the spatial frequencies for the x and y directions. Accordingly, in frequency space the image includes a plurality of isolated peaks at different locations depending on the 2-D modulation pattern 104. Similar peaks (for a modulation pattern not rotated at 45°) are schematically shown in FIG. 15A. One of these peaks may be isolated to obtain wavefront information along one direction and another peak may be isolated to obtain wavefront information along another direction as shown for the x direction in FIG. 15B, and in the y direction in FIG. 15C.

In certain embodiments, however, prior to performing the Fourier transform or otherwise obtaining a spatial frequency representation of the image, regions to be masked out at a later stage are identified as represented by a block 405 in FIG. 14. As discussed above, high intensity regions resulting, e.g., from glint or other reflection or scatter, may present difficulty in the processing of the images. Accordingly, in certain embodiments one or more areas in the image are identified that contain localized high intensity regions and a mask is applied to exclude at a later stage those areas from the analysis. The detection of these high intensity regions may be performed via a histogram analysis that yields a threshold value of intensity (see block 404). Such a histogram analysis may be based, for example, on a gray-scale histogram produced from the intensity values obtained by the detector array. This gray-scale histogram may be evaluated to determine a suitable grayscale threshold. Areas in the image which are above the grayscale threshold are identified as glint or other high intensity spots to be distinguished from the surrounding useable portions of the image. (In some embodiments, a low intensity threshold is determined and portions of the image which are below the grayscale threshold are identified as problem areas and are recorded for masking out.) A pixel mask may be generated which is used to exclude these problem areas from the image. This mask may be combined with other masks such as a mask that blocks portions outside the pupil as described above. The mask may be applied at a later stage in the processing.

After creating the glint or high-intensity mask and producing a frequency space representation of the image, intensity peaks in the spatial frequency mapping are isolated as discussed above and illustrated in FIGS. 15A and 15B. The selection of separate peaks e.g., on the $f_x$ and $f_y$ axis, are indicated by blocks 408a, 408b and blocks 410a, 410b in FIG. 14 for subsequent determination of wavefront shape in respective to the x and y directions. Blocks 408a, 408b as well as blocks 410a, 410b are shown in separate X and Y branches 409a, 409b in FIG. 14 to indicate that the process is carried out for both X and Y.

The peaks will generally be located on the $f_x$ and $f_y$ axes for two-dimensional gratings oriented along x and y directions. In the case where the periodic diffractive element is rotated, for example, by about 45° with respect to the x and y axis, the peaks will be off-center from the $f_x$ and $f_y$ axes. Exemplary peaks for a rotated 2D sinusoidal pattern rotated by 45° are represented by the following expressions:

$$\delta(f_x - 1/p, f_y - 1/p) \otimes F\{e^{-jp\frac{\partial \phi}{\partial x'}}\} \quad (7a)$$

$$\delta(f_x + 1/p, f_y - 1/p) \otimes F\{e^{-jp\frac{\partial \phi}{\partial y'}}\} \quad (7b)$$

The exponential terms $$e^{-jp\frac{\partial \phi}{\partial x'}}$$

and $$e^{-jp\frac{\partial \phi}{\partial y'}},$$

can be isolated by transforming the peak in frequency space back into the spatial domain. Accordingly, the two-dimensional inverse Fourier transform may be applied to the pair of isolated peaks as indicated by blocks 412a, 412b.

The wavefront information, e.g., the wavefront gradients $$\frac{\partial \phi}{\partial x'}$$

and $$\frac{\partial \phi}{\partial y'},$$

can be extracted from the exponential terms using the arctangent function (ArcTan[ ]) which obtains the phase $\theta$ of a complex exponential, $|M|e^{-j\theta}$, where $|M|$ is the magnitude.

(The phase θ referred to in connection with the complex exponential |M|e$^{-j\theta}$ which may be represented in phaser form is to be distinguished from the phase, φ, of the wavefront. Here the phase θ of the complex exponentials is equal to $$p\frac{\partial \phi}{\partial x'}$$

and $$p\frac{\partial \phi}{\partial y'})$$

The arctangent may be used to determine the phase θ and thus the gradient terms $$\frac{\partial \phi}{\partial x'}$$

and $$\frac{\partial \phi}{\partial y'}$$

as represented by blocks 414a and 414b.

Figure 16A:
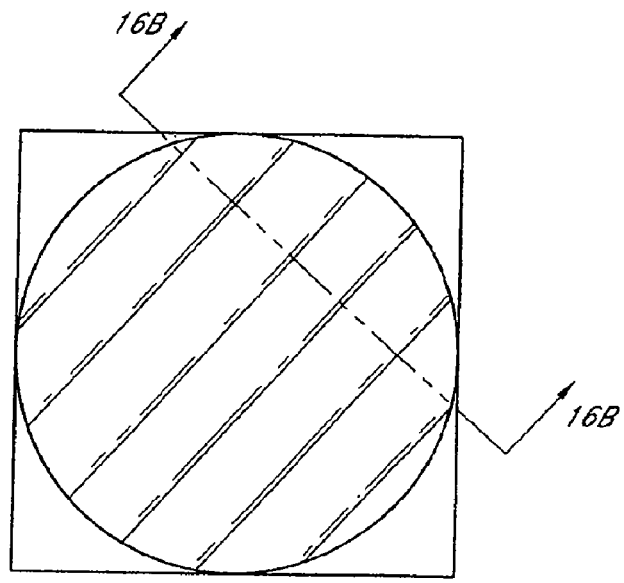
FIG. 16A is a schematic view of a three-dimensional plot of the gradient of the wavefront extracted via processing shown in FIG. 14 prior to phase unwrap.
Figure 16B:
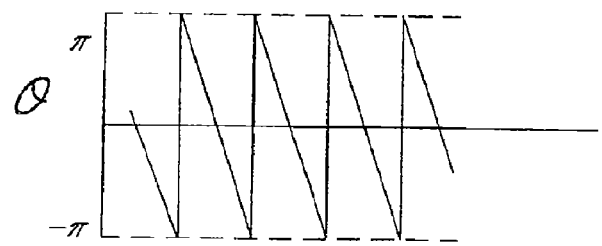
FIG. 16B is a cross-sectional view of the plot in FIG. 16A taken along the line 16B-16B and showing the $-\pi$ to $+\pi$ range of values prior to phase unwrap.

The arctangent function, however, ranges from −π to +π. Accordingly, the gradient information is limited to these values as illustrated by FIG. 16A which shows an exemplary gradient mapping produced by taking the arctangent function as described above. FIG. 16B depicts a cross-section through the map in FIG. 16A along the line 16B-16B. As shown, the mapping includes a plurality of sections where the values $$\left(e.g., p\frac{\partial \phi}{\partial x'}\right)$$

extend from −π to +π. In various preferred embodiments, the complex phase values are modified to extend beyond the limited range between −π and +π. Blocks 418a and 418b in FIG. 14 represent this processing. Using algorithms referred herein to as phase unwrap algorithms, the progression of phase θ beyond this range from −π to +π may be obtained. Various phase unwrapping techniques and algorithms are well known in the art and may be employed. In certain embodiments, for example, if the change in phase θ is larger than +π between a pair of pixels adjacent along, e.g., a row, then +2π is subtracted from the phase value θ. Similarly, if the change in phase θ is smaller (more negative) than −π between a pair of adjacent pixels along, e.g., a row, than −2π is added to the phase value θ. Similarly, this algorithm may be employed down the columns considering the average phase values across a row and for example, subtracting +2π (or adding −2π) to each pixel in the row if the change in average phase θ for the row is larger than +π (or more negative than −π). Variations in phase unwrapping techniques and algorithms are possible.

The phase unwrap is susceptible to introducing error in the image in the case where pixels have low signal-to-noise values. In this region of signal-to-noise or low contrast, the edge of the diffractive element is blurred. This low contrast coincides with a low magnitude value (|M| in the complex exponential, |M|e$^{-j\theta}$) of the exponential terms $$e^{-jp\frac{\partial \phi}{\partial x'}}$$

extracted, e.g., by inverse Fourier transform, as described above. Low contrast corresponds to low signal-to-noise, which means that the phase term θ is noisy. Noise in the phase term can cause the phase term θ to vary anywhere between −π to +π. Application of the phase unwrap algorithm to a noisy region may result in erroneous values not only for the noisy pixel(s) but other pixels as well. These "phase unwrap errors," therefore, interfere with accurate reconstruction of the wavefront. To address this problem, in various preferred embodiments, the noisy low contrast pixels that may cause phase unwrap error are masked out.

As illustrated by block 413b in FIG. 14, one or more areas in the image are identified that contain low contrast or low signal-to-noise and a mask is created for reducing or excluding the contribution of those areas from the analysis. The noisy/low contrast pixels may be identified after the inverse Fourier transform is applied and before the phase unwrap or even after the determination of the phase as shown in FIG. 14. The detection of these noisy regions may be performed via a histogram analysis that yields a threshold value, for example, of contrast, noise, or signal-to-noise. Such a histogram analysis may be based on the magnitude value (|M| in the complex exponential, |M|$^{-ej\theta}$) of the exponential terms $$e^{-jp\frac{\partial \phi}{\partial x'}}$$

extracted, e.g., by inverse Fourier transform, as described above. This histogram may be evaluated to determine a suitable threshold as represented by block 413b. Alternatively, thresholds other than those obtained from a histogram-type or comparative analysis may be employed. Pixels having a corresponding magnitude value below the threshold are identified as noisy to be distinguished from the surrounding useable portions of the image. A pixel mask referred to as a signal-to-noise or contrast mask may be generated, which is used to attenuate or exclude contributions from those noisy or low contrast areas from the image. This mask may be combined with other masks as represented by line 411b and circle 415b, such as a mask that blocks portions outside the pupil, or the intensity threshold (or glint) mask as describe above with respect to block 405.

As illustrated by circle 415b and arrow extending from flow path 416 in FIG. 14, the one or more masks may be applied one or more times at various stages of the process. In various embodiments, for example, the mask may be applied prior to the phase unwrap (block 418a, 418b in FIG. 14). A composite mask may be formed by combining any of the masks described herein and/or other types of masks. Circle 415b schematically represents combining of the masks. In certain embodiments, the mask include values of "0" for regions to be masked out and is multiplied with the data set to implement the masking process. The mask may otherwise reduce the affects of problem areas.

As indicated in FIG. 14, several steps applicable to both X and Y branches 409a, 409b are shown only for the Y branch.

A dashed box 417 in FIG. 14 includes portions of the flow chart that are replicated for the X branch 409a as well.

After this processing the wavefront may be reconstructed as illustrated by block 420, by determining the wavefront shape from gradient information and by combining the x and y components. The mask may be applied at this stage as well as indicated by an arrow extending from flow path 416 to block 420. The wavefront can be reconstructed using known algorithms for solving multi-dimensional partial differential equations including but not limited to "Successive Over-relaxation" and finite-element analysis.

A reference wavefront corresponding to the wavefront obtained by measuring a perfectly flat wavefront, perfect eye or optical element may be subtracted from the wavefront measured as illustrated by block 422 in FIG. 14. This reference wavefront will contain contributions of aberration from the wavefront sensor and thus subtracting out the reference wavefront may reduce errors contributed by imperfections in the wavefront sensor optics.

The last block 424 represents employing least square fitting for example to Zernike polynomials as described above to obtain a representation of the wavefront. The mask may also be applied at this stage in some embodiments as indicated by the arrow extending from flow path 416 to block 424. Accordingly, as illustrated by the block diagram in FIG. 14, the mask may be applied at a stage so as to attenuate the contribution or exclude the particular area from the phase unwrap, wavefront reconstruction, and Zernike polynomial fitting portions of the analysis algorithm. The masks may, however, be applied at different stages in different embodiments. Other variations are possible.

Figure 17:
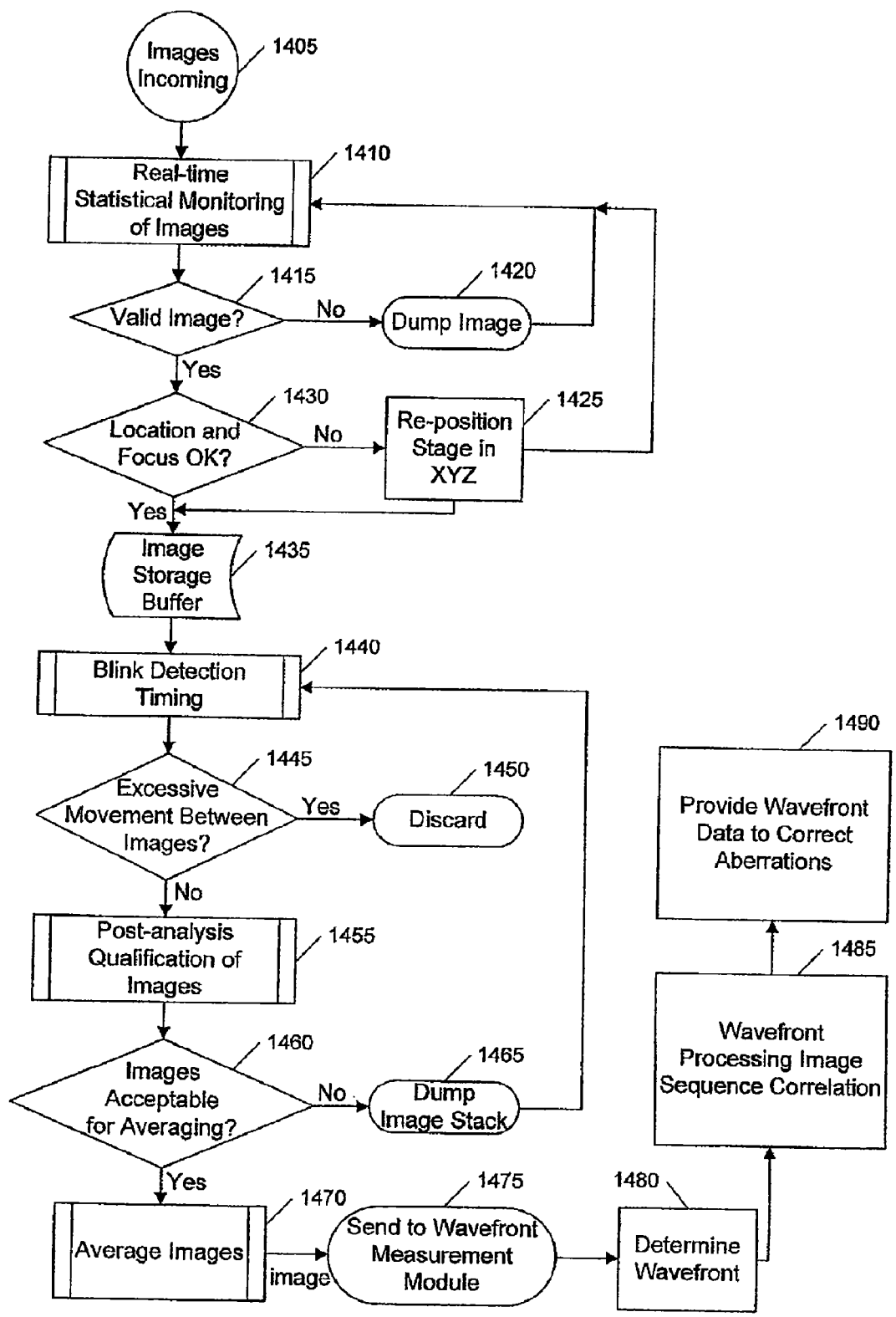
FIG. 17 is a flow diagram illustrating additional wavefront image processes.

In certain embodiment of the invention, real-time or near real-time analysis of images created with the wavefront sensor can identify problems in the images, provide closed loop feedback of positional information to the XYZ stage 246 to center the pupil in the image frame, set the focus, and analyze captured images or sets of images to determine outliers before averaging. A process flow diagram in FIG. 17 illustrates methods for monitoring images created with a wavefront measuring system such as the binocular instrument 300. The methods can be implemented and used as a single method for monitoring images, or as one or more separate methods. In one embodiment, the methods for determining which images should be used for calculating a wavefront are implemented in an image monitoring module in the data processor.

Referring to FIG. 17, at state 1405 images are received as input for processing. For example, the images can be provided to the data processor from the wavefront sensor or from another source, e.g., images stored on a computer storage medium (e.g., tape, CD, DVD, other optical disk, magnetic disk, or RAM). At state 1410, the process performs real-time or near real-time statistical monitoring of the images to determine the location of the pupil in the image, the pupil diameter, and the quality of the image. The statistical monitoring process incorporates various image processing techniques to detect erroneous results occurring from incorrect XYZ positioning of the sensor, eye movement, tear film, eye blinks, eyelashes, glint, artifacts, and spurious or uncontrolled accommodation.

In one embodiment, during statistical monitoring the process segments a wavefront image using a histogram based approach to identify the pupil from the background of the image. The process stores values that represent attributes of the image, e.g., the diameter of the pupil, the location of the pupil within the image frame, and whether the image contains a saturated spot, a bright spot or glint (or other undesirable image characteristics which can be detrimental to the wavefront analysis). At state 1415, the process evaluates the outcome results of state 1410 to determine whether the image is a valid or invalid image. For example, the image can be an invalid image if it contains a saturated spot, a bright return or glint, or if the image is otherwise of poor quality. If the image is invalid, the process moves to a state 1420 and discards the image from the analysis. From state 1420, the process moves to state 1410 and proceeds as described above.

After the process evaluates whether an image is valid in state 1415, the process moves to a state 1430 and checks the location of the pupil and the focus of the image. In one embodiment, the process determines the pupil location by comparing a predetermined desired pupil location in an image (usually near or at the center of the image) to the actual pupil location (e.g., the XY coordinates of the pupil determined in state 1410) of the image being evaluated. If the values representing the actual location of the pupil in the image and the desired location of the pupil in the image deviate by a predetermined amount, the process moves to a state 1425 and commands the XYZ stage to move to a new X and/or Y position so that in subsequent images the pupil will be closer to the center or in the center of the image "frame." The process creates the next image at the new location of the stage and processes the image as described herein. If the location of the pupil in the image deviates from the center of the image excessively so that the pupil is un-usable for determining a wavefront measurement (e.g., the pupil is not completely in the image), the stage is re-positioned in state 1425, the image is discarded and the process moves to state 1410 where it continues to monitor incoming images. If the location of the pupil in the image does not deviate by an amount such that the image is un-usable, the process can re-position the stage in state 1425 if necessary, the image is not discarded, and the process moves to state 1435.

In one embodiment, the process controls the focus of the image via an algorithm implemented in an image monitoring module in the data processor. The process controls focus by checking if a first image is in focus by determining the sharpness of the imaged pupil using various image processing techniques, e.g., analyzing high-frequency spatial components in the image. If the first image is out of focus, the process moves the Z axis of the XYZ stage a small amount in one direction to a new Z position. A second image is generated at the new Z position and the process analyzes this image to determine if the second image is more or less sharp. If the second image is sharper, the XYZ stage continues to move in the same direction as before and subsequent images are analyzed for sharpness until the sharpness of an image passes a predetermined sharpness threshold. If the second image became less sharp or un-focused after the stage movement, the process changes the direction of the XYZ stage and the stage moves in this new direction as subsequent images are generated. The stage continues to move until the subsequent images are in focus, e.g., pass a sharpness threshold. Alternatively, two images can be generated at two Z-axis locations of the wavefront sensor XYZ stage, and then those images can be compared to determine which one is sharper. Following this comparison, the process generates other images while moving the XYZ stage in the direction of the sharper image, until the process determines that the images pass the focus or sharpness threshold. If, after the initial stage movement, the image becomes more out of focus the stage changes direction and continues moving until the subsequent images are in focus. If the image is out of focus by a predetermined amount making the image unusable for calculating an accurate wavefront measurement, the image is discarded, and the process moves to state 1410, and proceeds as described above.

If the focus of a valid image is acceptable at state 1430, the process moves to state 1435 where one or more of the images of a pupil, e.g., a series of images, are stored in an image storage buffer, as in "image stack." The image stack can be a sequential series of images, or can be a series of images of an eye that are not sequential because of, for example, intermittent invalid images. At state 1440, the process compensates for a patient's blinking by removing images that were generated during a certain time period after the patient blinked. This compensation can improve the quality of the images used for wavefront measurements. Detecting when a patient blinks and determining the appropriate image acquisition timing to compensate for the blinks can be accomplished based on the output of the above process. In state 1440 the process performs blink detection timing to capture images from the same point in time after a blink. When a patient blinks, the image is of poor quality because the pupil is either partially or completely obscured by the eyelid and the image is thus is deemed invalid by, for example, the above-described process. Wavefront images of the pupil taken too soon or too long after a blink can also be erroneous. A contributor to erroneous wavefront measurements is the eye's tear film, which typically degrades and dries out over time after a blink. If images are taken following a suitable delay period after a blink, the eye has a chance to stabilize. The delay period should not be so long that the tear film has begun to dry out or break down. During blink compensation, the process monitors the elapsed time between when the eye blinks and selects images generated after the eye has stabilized but before it dries out.

In one embodiment, a series of wavefront images is analyzed to identify an image that depicts a pupil at least partially obscured by an eyelid during a blink of the eye. This analysis may be part of the analysis conducted to determine valid images, or it may be conducted by another suitable image analysis process. The series of wavefront images is then further analyzed to identify another image that is generated after the eye has completed the blink such that this later generated image depicts a non-obscured pupil. In some embodiments, the identified image is the first image in the series of images that depicts a non-obscured pupil subsequent to the image depicting an at least partially obscured pupil. This image depicting a non-obscured pupil (e.g., a valid image), and/or valid images generated subsequent to this first image, can be stored and used for subsequent processing (e.g., determination of excessive movement between images, post-analysis qualification of images, averaging the images and determining a wavefront measurement).

In some embodiments, the process determines which images to store for further processing based on a predetermined time interval after blinking. For example, a timer can start after the process identifies a valid image depicting a non-obscured pupil in a series of wavefront images that were taken during the blink of an eye, and one or more of the images generated subsequent to the identified image are stored to a buffer at a specific interval after the blink occurs. For example, the time interval can be, e.g., less than 0.10 seconds, or equal to or between (in seconds) 0.10-0.20, 0.20-0.30, 0.30-0.40, 0.40-0.50, 0.50-0.60, 0.60-0.70, 0.70-0.80, 0.80-0.90, 0.90-1.00, 1.00-1.10, 1.10-1.20, 1.20-1.30, 1.30-1.40, 1.40-1.50, 1.50-1.60, 1.60-1.70, 1.70-1.80, 1.80-1.90, 1.90-2.00, 2.00-2.10, 2.10-2.20, 2.20-2.30, 2.30-2.40, 2.40-2.50, 2.50-2.60, 2.60-2.70, 2.70-2.80, 2.80-2.90, 2.90-3.00, 3.00-3.10, 3.10-3.20, 3.20-3.30, 3.30-3.40, 3.04-3.50, 3.50-3.60, 3.60-3.70, 3.70-3.80, 3.80-3.90, 3.90-4.00, or greater than 4.00 seconds. In one preferred embodiment, the time interval is about 1.00 seconds. With this process running, a patient can look into the wavefront measurement instrument and blink normally, eliminating the possibility of capturing images during, or directly after a blink which might contaminate the data. The images identified for analysis are therefore from about the same point in time after a blink. Images that do not meet the timing criteria can be discarded from the analysis. In an alternative embodiment, the process determines which images to store for further processing based on the number of images generated after determining that an image depicts a non-obscured pupil.

Moving to a state 1445, the process analyzes images to determine whether the movement of the pupil in successive images exceeds predetermined criteria. The pupil can move due to saccades or another eye movement. Excessive pupil movement can compromise the wavefront measurement. In one embodiment, the process determines the amount of movement of the pupil by analyzing the stored XY location of the pupil in each image of a stored stack of related images, and determines if the movement exceeds the criteria. If in state 1445 the process determines that there is excessive movement of the pupil, the process moves to a state 1450 wherein the image is discarded from the analysis and the next image in the stack of related images is analyzed. In state 1445, if the process determines that the movement of the pupil is not excessive, the image can be used for further processing, including determining a wavefront measurement of the aberrations of the eye, and the process moves to a state 1455.

At state 1455, the process stores the images that are to be used for further processing in a buffer as an image set or stack, and the images are further evaluated to determine if they should be combined to form an "average" image. The process will subsequently determine a wavefront measurement from the averaged image. Images are averaged to help remove image noise, for example, camera noise. At state 1455, the process performs further analysis of the images to determine if the images in the image set are "like" images, before they are averaged in state 1470. For example, the process can perform blob analysis to determine if the pupil is round or if there is a major inclusion in an imaged pupil, such as an eyelash or droopy eyelid. Opaque anomalies in an image such as cataracts, floaters, etc. can also be identified using image processing techniques, and these anomalies can be subsequently masked out so they do not affect forming the averaged image. Also, the identified anomalies can also be provided to the operator to alert the operator and patient to certain conditions that are present in the patient's eye. For example, the instrument can be used for early detection of cataracts, where a cataract appears as a dark spot in the image displayed to an operator, and/or the cataract is identified by image processing software as an anomaly that requires further investigation.

Following image qualification, the process moves to a state 1460 wherein the process determines whether the stored images in a set are acceptable for averaging. If they are acceptable, the process moves to state 1470 where the images are averaged and the process provides the resulting image to a wavefront measurement module for wavefront characterization such as described above. In one embodiment, the images are averaged by adding together the values of like pixels (e.g., pixels corresponding to the same eye position) of each image in the image set and dividing by the number of images. If the process determines in state 1460 that the set of images is not acceptable for averaging, the process moves to state 1465 where the image stack is discarded from further processing, and then the process returns to state 1440 to process another series of images.

In state 1475 the process sends the image resulting from the averaging process to the wavefront measurement module. At state 1480, the wavefront measurement module determines a wavefront measurement using processes such as described above. As discussed above, processing of Talbot images is also described, for example, in U.S. Pat. No. 6,781,681 issued to Horwitz, titled "System and Method for Wavefront Measurement."

At state 1485, the process performs wavefront processing image sequence correlation. Here, the process compares the wavefronts from two or more average images (e.g., from two or more sets of images) to determine how similar the wavefronts are to each other and identify anomalies which were not identified in the previous processes. For example, problems relating to spurious accommodation, tear film and gaze angle can be determined by image sequence correlation. In one embodiment, wavefront processing image sequence correlation can be performed by analyzing each of the image stacks completely through the wavefront processing and comparing the wavefronts or Zernike polynomial representation. In an alternative embodiment, wavefront processing image sequence correlation can be performed on a partially processed sequence of images at any intermediate stage, such as in a Fourier space stage of processing the images. For example, wavefront data can be quickly processed to determine FFT's, and the FFT's can be compared to determine the similarity of the wavefronts. After correlating two or more wavefronts, at state 1490 the process provides the wavefront data for use to, for example, create a lens or for eye surgery to correct for the aberrations identified by the wavefront data.

Variations in the processing, however, are possible. The processing described above or portions thereof may be employed, may be excluded, or may be combined together with other techniques in different embodiments. The order of processing steps may vary as well.

Advantageously, various systems and methods described herein may be used to measure waveshaping properties including the aberrations of lens and/or of the eye Such measurement may be implemented using cost effective, highly accurate apparatus and methods. Various embodiments of the measurement instrument are designed specifically to meet requirements of eye-care and eyewear fabrication professionals, and at the same time to be affordable so that the instrument can be deployed in offices and facilities throughout the world. Embodiments of the invention can be implemented in relatively simple instrument designs that can reduce costs. As a result, ocular measurement using a wavefront sensor may therefore be a widely used technology for the benefit of eye care. The instrument may be used over the widest possible patient population, with special emphasis on diagnosing vision problems and abnormalities in children.

Higher order aberrations may also be measured with this wavefront sensor technology. Such higher-order aberrations can be generated by the lens manufacturing process. Knowledge of these higher-order aberrations therefore may be useful in implementing improved vision correction. Knowledge of higher order aberrations in the eye may also be useful in providing better correction.

Various techniques and designs disclosed herein may further increase the accuracy, precision, and dynamic range of the optical measurements. For example, illumination and filtering techniques may be employed to improve the results obtained.

The apparatus and methods described above, however, are only exemplary. Accordingly, the structures and processes employed should not be limited to those embodiments specifically recited herein. For example, the structures may include additional or different components and may not include all the features described herein. Processing may also be added or processing may be excluded or otherwise altered. The order of the process may be varied.

Moreover, those skilled in the art will appreciate that the methods and designs described above have additional applications and that the relevant applications are not limited to those specifically recited above. The present invention may be embodied in other specific forms without departing from the characteristics as described herein. The embodiments described above are to be considered in all respects as illustrative only and not restrictive in any manner.

What is claimed is:

1. A lensometer for measuring waveshaping properties of a spectacle lens across at least a portion of the spectacle lens, the lensometer comprising:
   a light source for emitting light;
   beam-tailoring optics that receives light from said light source and outputs a light beam having a beam size at least as large as said portion of said spectacle lens to be measured, said light source, said beam-tailoring optics, and said spectacle lens disposed along an optical path such that said light beam propagates through said spectacle lens, wherein said beam is expanded so as to increase said beam width from between about 10 to 20 millimeters to between about 20 to 80 millimeters; and
   a Talbot plane self-imaging wavefront sensor disposed in said optical path to receive said light beam after said beam has passed through said spectacle lens, said Talbot plane self-imaging wavefront sensor configured for use in determining the waveshaping properties of the spectacle lens based at least in part on a near field diffraction pattern.

2. The lensometer of claim 1, wherein said beam-tailoring optics comprises a beam-expander for increasing the lateral spatial extent of the light beam.

3. The lensometer of claim 2, wherein said beam-tailoring optics provides a beam size between about 45 and 65 millimeters in width and 20 and 65 millimeters in height.

4. The lensometer of claim 1, wherein said beam-tailoring optics comprises collimating optics for producing a substantially collimated beam.

5. The lensometer of claim 1, further comprising an obstruction positioned in said optical path to produce a region on said spectacle lens having reduced illumination to decrease retro-reflection from said spectacle lens into said Talbot plane self-imaging wavefront sensor.

6. The lensometer of claim 5, wherein said obstruction comprises a central obstruction in said optical path to produce a central obscuration in said light beam incident on said spectacle lens.

7. The lensometer of claim 1, further comprising null optics in said optical path.

8. A method of measuring waveshaping properties of a spectacle lens across at least a portion of the spectacle lens, the method comprising:
   propagating a beam through said spectacle lens;
   propagating said beam, having passed through said spectacle lens, through at least one two-dimensional modulation pattern thereby producing a near field diffraction pattern at a Talbot plane;
   imaging said near field diffraction pattern at said Talbot plane; and
   determining a measure of said waveshaping properties of said spectacle lens based at least in part on said near field diffraction pattern,
   wherein said beam is expanded so as to increase said beam width from between about 10 to 20 millimeters to between about 20 to 80 millimeters.

9. The method of claim 8, wherein said beam has a beam size at least as large as said portion of said spectacle lens to be measured.

10. The method of claim 9, further comprising expanding said beam such that said beam size is at least as large as said portion of said spectacle lens to be measured.

11. The method of claim 10, wherein said beam is expanded prior to passing said beam through said spectacle lens.

12. The method of claim 10, wherein prior to expanding the beam, the method comprises:

propagating the beam through said spectacle optics; and reflecting the beam from a diffusely reflecting surface.

13. The method of claim 12, wherein said beam is propagated through said spectacle lens after said beam is expanded.

14. The method of claim 8, further comprising collimating said beam prior to passing said beam through said spectacle lens.

15. The method of claim 8, further comprising re-shaping the spectacle lens in response to said measurement of waveshaping properties.

16. The method of claim 8, further comprising removing said spectacle lens from the path of the beam and measuring an eye having a cornea, pupil, and lens, removing said spectacle comprising:

moving a lens holder holding said spectacle lens in place; and relocating beam expanding elements such that said beam incident on said eye is smaller than the pupil of said eye, wherein said beam is propagated through said spectacle lens when said spectacle lens is worn by a user such that said beam enters an eye of the user.

17. The method of claim 16, further comprising displacing said beam laterally with respect to said eye such that light from said beam which is reflected from said cornea is deflected at an angle thereby reducing error in said measurement of said waveshaping properties of said eye.

18. The method of claim 16, further comprising introducing a dark region in said beam, said dark region disposed with respect to said eye so as to reduce retro-reflection.

19. The method of claim 17, wherein said beam has a substantially annular intensity cross-section.

* * * * *